(12) United States Patent
Hosokawa et al.

(10) Patent No.: US 11,480,559 B2
(45) Date of Patent: Oct. 25, 2022

(54) BLOOD COLLECTION TUBE, REAGENT, AND METHOD FOR ANALYZING BLOOD CHARACTERISTICS USING SAME

(71) Applicant: FUJIMORI KOGYO CO., LTD., Tokyo (JP)

(72) Inventors: Kazuya Hosokawa, Tokyo (JP); Tomoko Wada, Tokyo (JP); Hisayo Kaneko, Tokyo (JP); Takaaki Hasegawa, Tokyo (JP); Tomoka Nagasato, Tokyo (JP)

(73) Assignee: FUJIMORI KOGYO CO., LTD., Tokyo (JP)

(*) Notice: Subject to any disclaimer, the term of this patent is extended or adjusted under 35 U.S.C. 154(b) by 108 days.

(21) Appl. No.: 16/068,379

(22) PCT Filed: Jan. 6, 2017

(86) PCT No.: PCT/JP2017/000335
§ 371 (c)(1),
(2) Date: Jul. 6, 2018

(87) PCT Pub. No.: WO2017/119508
PCT Pub. Date: Jul. 13, 2017

(65) Prior Publication Data
US 2019/0004031 A1    Jan. 3, 2019

(30) Foreign Application Priority Data

Jan. 7, 2016  (JP) .............................. JP2016-002012
Mar. 1, 2016  (JP) ................................. 2016-039240

(51) Int. Cl.
*G01N 33/49*    (2006.01)
*G01N 33/86*    (2006.01)
(Continued)

(52) U.S. Cl.
CPC ..... *G01N 33/4905* (2013.01); *A61B 5/15003* (2013.01); *A61B 5/154* (2013.01);
(Continued)

(58) Field of Classification Search
CPC .... G01N 33/4905; G01N 11/16; G01N 33/48; G01N 33/86; A61B 5/15003; A61B 5/150755; A61B 5/154; C12Q 1/34
See application file for complete search history.

(56) References Cited

U.S. PATENT DOCUMENTS 3,814,248 A  *  6/1974  Lawhead ............ B01L 3/50215
                                                        210/789
5,213,765 A      5/1993  Kasai et al.
(Continued)

FOREIGN PATENT DOCUMENTS

CN    1761876 A    4/2006
JP    4-9143       1/1992
(Continued)

OTHER PUBLICATIONS

Swartz et al., "Isolation and Characterization of Trypsin Inhibitor from Opaque-2 Corn Seeds", The Journal of Biological Chemistry, vol. 252, No. 22, Nov. 25, 1977, pp. 8105-8107.
(Continued)

*Primary Examiner* — Brian J. Sines
(74) *Attorney, Agent, or Firm* — Marshall, Gerstein & Borun LLP

(57) ABSTRACT

A method for analyzing thrombogenic capacity or blood coagulation capacity, the method comprising adding calcium, a blood coagulation factor XII (FXII) inhibitor, and a kallikrein inhibitor to blood collected with a blood collection tube containing sodium citrate, to allow initiation of blood coagulation reaction, is provided. Preferably, heparin, heparan sulfate, and tissue factor are further added to the blood, (Continued)

and thrombogenic capacity or blood coagulation capacity is analyzed.

19 Claims, 17 Drawing Sheets

(51) Int. Cl.
    *A61B 5/15*         (2006.01)
    *G01N 33/48*       (2006.01)
    *C12Q 1/34*        (2006.01)
    *A61B 5/154*       (2006.01)
    *G01N 11/16*       (2006.01)
    *C12N 9/99*        (2006.01)

(52) U.S. Cl.
    CPC .......... *A61B 5/150755* (2013.01); *C12Q 1/34* (2013.01); *G01N 11/16* (2013.01); *G01N 33/48* (2013.01); *G01N 33/86* (2013.01); *A61B 5/150351* (2013.01); *C12N 9/99* (2013.01); *G01N 2333/7454* (2013.01); *G01N 2333/8117* (2013.01); *G01N 2333/96455* (2013.01); *G01N 2333/96458* (2013.01)

(56) References Cited

U.S. PATENT DOCUMENTS

| | | | | |
|---|---|---|---|---|
| 5,472,850 | A * | 12/1995 | Morrissey | G01N 33/68 435/13 |
| 8,609,632 | B2 * | 12/2013 | Shriver | A61P 7/02 514/56 |
| 2003/0044876 | A1 * | 3/2003 | Stief | C12Q 1/37 435/23 |
| 2006/0171915 | A1 | 8/2006 | Okamoto et al. | |
| 2009/0311675 | A1 * | 12/2009 | Hosokawa | G01N 33/86 435/5 |
| 2010/0248329 | A1 * | 9/2010 | Okamoto | A61B 5/150015 435/212 |
| 2010/0267066 | A1 * | 10/2010 | Hosokawa | B01F 13/0059 435/13 |
| 2010/0316724 | A1 * | 12/2010 | Whitfield | A61P 37/06 424/489 |
| 2011/0151500 | A1 | 6/2011 | Hosokawa et al. | |
| 2012/0231485 | A1 * | 9/2012 | Onundarson | G01N 33/86 435/13 |
| 2012/0301966 | A1 | 11/2012 | Hosokawa et al. | |
| 2013/0209444 | A1 | 8/2013 | Dockal et al. | |
| 2014/0220552 | A1 * | 8/2014 | Moskowitz | G01N 33/86 435/2 |
| 2014/0275061 | A1 * | 9/2014 | Orwat | A61P 7/02 514/230.8 |
| 2015/0344862 | A1 | 12/2015 | Schellenberger et al. | |
| 2017/0023596 | A1 * | 1/2017 | Hosokawa | G01N 33/86 |

FOREIGN PATENT DOCUMENTS

| | | |
|---|---|---|
| JP | 2000-083934 A | 3/2000 |
| JP | 2015-052015 A | 3/2015 |
| JP | 2015-509923 A | 4/2015 |
| WO | WO-2007/046450 A1 | 4/2007 |
| WO | WO-2009/069656 A1 | 6/2009 |
| WO | WO-2010/018833 A1 | 2/2010 |
| WO | WO-2010/091122 A1 | 8/2010 |
| WO | WO-2011/099569 A1 | 8/2011 |
| WO | WO-2013/116366 A1 | 8/2013 |
| WO | WO-2015/156322 A1 | 10/2015 |

OTHER PUBLICATIONS

Partial Supplementary European Search Report in EP Application No. 17736045.0 dated Sep. 6, 2019, 9 pages.

International Preliminary Report on Patentability and Written Opinion in International Application No. PCT/JP2017/000335 dated Jul. 19, 2018, 10 pages.

International Search Report in International Application No. PCT/JP2017/000335 dated Feb. 21, 2017, 2 pages.

Office Action in CN Application No. 201780005964.7 dated Mar. 10, 2021, 50 pages.

Hearing Notice in IN Application No. 201847028881 dated Jan. 6, 2022, 2 pages.

* cited by examiner

BLOOD COLLECTION TUBE, REAGENT, AND METHOD FOR ANALYZING BLOOD CHARACTERISTICS USING SAME

TECHNICAL FIELD

The present invention relates to a blood collection tube and a reagent which can be suitably used for analysis of blood properties such as the platelet thrombus formation capacity and the mixed white thrombus formation capacity, and a method for analyzing blood properties using them.

BACKGROUND ART

Blood tests often cannot be carried out immediately after blood collection, and coagulation of blood occurs after a certain length of time. Thus, blood collection is carried out using a blood collection tube in which an anticoagulant such as heparin or sodium citrate is placed therein. Examples of blood collection tubes using heparin as an anticoagulant include the one disclosed in Patent Document 1.

In thrombus formation or hemostatic reaction in the body, primary hemostasis including platelet adhesion to collagen and aggregation reaction, and secondary hemostasis caused by fibrin gel produced by the activation of blood coagulation factors, simultaneously occur. Under arterial conditions, primary hemostasis, which is mainly based on platelet aggregation reaction, becomes dominant, while under venous conditions, secondary hemostasis, which is based on blood coagulation reaction, becomes dominant over primary hemostasis, leading to formation of thrombi containing a larger amount of fibrin. The present inventors have developed analyzers for blood properties using a microchip having a channel mimicking a blood vessel which allows evaluation of the platelet thrombus formation capacity and the mixed white thrombus formation capacity using a small amount of blood (Patent Documents 2 to 5).

As devices for detailed analysis of blood coagulation reaction in the absence of blood flow, thromboelastograph (TEG), ROTEM (trademark), and the like have been used.

PRIOR ART DOCUMENTS

Patent Documents

[Patent Document 1] JP 4-9143 A
[Patent Document 2] Japanese Translated PCT Patent Application Laid-open No. 2010/018833
[Patent Document 3] Japanese Translated PCT Patent Application Laid-open No. 2011/99569
[Patent Document 4] Japanese Translated PCT Patent Application Laid-open No. 2009/69656
[Patent Document 5] Japanese Translated PCT Patent Application Laid-open No. 2007/46450

SUMMARY OF THE INVENTION

Problems to be Solved by the Invention

As described above, blood collection tubes containing therein an anticoagulant such as heparin have been known, but the known blood collection tubes still remain to be improved since, for example, contact of blood to the cap of a blood collection tube causes activation reaction of contact factors in the coagulation cascade. Further, for evaluation of collected blood using the above-described analyzers for blood properties, more customized blood collection tubes have been demanded.

Also for use of a conventional, widely used blood collection tube containing citric acid, development of a reagent that enables analysis of the mixed white thrombus formation capacity and a blood coagulation test more sensitively has been demanded.

Means for Solving the Problems

The present inventors discovered that even a generally widely used vacuum blood collection tube containing an anticoagulant such as heparin or sodium citrate causes activation of contact factors, leading to promotion of blood coagulation in whole blood, and that the promotion of coagulation can be suppressed by preliminarily including a small amount of a contact factor inhibitor such as a blood coagulation factor XII (FXII) inhibitor or a kallikrein inhibitor in the blood collection tube. The present inventors also discovered that blood collected with such a blood collection tube containing therein heparin (preferably low-molecular-weight heparin) or sodium citrate, and a contact factor inhibitor, can be suitably used for analysis of the platelet thrombus formation capacity and the mixed white thrombus formation capacity, and for conventional blood coagulation tests (ROTEM, TEG, and the like).

The present inventors also discovered that, in cases where a conventional, widely used blood collection tube containing citric acid is used, addition of an FXII inhibitor such as corn-derived trypsin inhibitor (CTI); a kallikrein inhibitor; and preferably together with a small amount of heparin and/or heparan sulfate; to the reagent enables favorable analysis of the mixed white thrombus formation capacity and conventional blood coagulation tests (ROTEM, TEG, and the like), thereby completed the present invention.

The present invention provides a blood collection tube containing therein heparin or sodium citrate, and a contact factor inhibitor such as a blood coagulation factor XII (FXII) inhibitor or a kallikrein inhibitor.

The heparin to be used herein may be a low-molecular-weight heparin or pentasaccharide (the pentasaccharide structure in heparin, which promotes Xa inhibition by antithrombin). The heparin is preferably a low-molecular-weight heparin having a mass average molecular weight of 4500 to 6500, and the low-molecular-weight heparin is preferably applied in the blood collection tube such that the amount of low-molecular-weight heparin in blood becomes 0.1 to 10 units/mL (0.1 to 10 IU (international units)/mL) upon blood collection. As an alternative to the heparin, heparan sulfate may be used. The FXII inhibitor is preferably corn-derived trypsin inhibitor (CTI), and the CTI is preferably applied in the blood collection tube such that the amount of CTI in blood becomes 5 to 50 µg/mL upon blood collection.

The kallikrein inhibitor is preferably aprotinin, and the aprotinin is preferably applied in the blood collection tube such that the amount of aprotinin in blood becomes 1 to 50 µg/mL upon blood collection.

The contact factor inhibitor such as an FXII inhibitor or a kallikrein inhibitor is preferably in a dry state after application to the inside of the blood collection tube.

The present invention also provides a method for analyzing the capacity to form a mixed white thrombus, which is mainly composed of fibrin and activated platelets, which method includes adding heparinase to blood collected using the blood collection tube containing therein heparin and a contact factor inhibitor, and then measuring the thrombogenic capacity. The heparinase herein is preferably added at a concentration of 1 to 10 units/mL (1 to 10 IU (international units)/mL). In one embodiment, the blood collection tube may contain therein not more than 25 μg/mL CTI and/or 1 to 50 μg/mL aprotinin, and heparinase may be added thereto together with not less than 10 μg/mL CTI. In a more preferred analysis method, blood is allowed to flow through a channel(s) mimicking a blood vessel(s) provided in a microchip, to perform the analysis. The microchip preferably has a portion(s) coated with collagen and tissue factor (tissue thromboplastin) on the channel(s). The blood may also be used for other blood coagulation tests such as ROTEM (trademark, rotation thromboelastometry) and TEG (trademark, Thromboelastography). In such cases, heparinase and low-concentration (for example, 0.1 nM to 10 nM) tissue factor are added to blood containing heparin and a contact factor inhibitor, to allow initiation of coagulation.

The present invention also provides a method for analyzing the capacity to form a platelet thrombus, which is mainly composed of activated platelets, which method includes allowing blood collected using the blood collection tube to flow through a channel(s) mimicking a blood vessel(s) provided in a microchip, the channel(s) having a channel-dividing section thereon, to measure thrombus formation.

The present invention also provides a method for analyzing thrombus formation in the presence of blood flow by addition of a contact factor inhibitor (FXII inhibitor, kallikrein inhibitor) and heparin (or heparan sulfate) to blood collected using a conventional blood collection tube having a rubber stopper, and a method for analyzing blood coagulation using ROTEM or TEG by addition of a contact factor inhibitor, heparin, and tissue factor.

Effects of the Invention

In cases where blood is preserved by anticoagulation treatment with heparin (preferably low-molecular-weight heparin) and a contact factor inhibitor(s) such as an FXII inhibitor (for example, corn-derived trypsin inhibitor (CTI)) and/or a kallikrein inhibitor (for example, aprotinin), platelet function can be maintained in good conditions, and the preserved blood is suitable for measurement of the platelet thrombus formation capacity in a microchip coated with collagen.

Further, in cases where blood is preserved by anticoagulation treatment with heparin and a contact factor inhibitor, and heparinase is added to the blood to degrade heparin, the resulting blood is suitable for measurement of the capacity to form a mixed white thrombus, which is mainly composed of fibrin and activated platelets, in a microchip coated with collagen and tissue factor.

Further, for example, in cases where blood is preserved by anticoagulation treatment with heparin and a kallikrein inhibitor, and heparinase and CTI are added upon the measurement, contact factors can be more strongly inhibited by both the kallikrein inhibitor and the CTI during the measurement, so that the resulting blood is suitable for measurement of the mixed white thrombus formation capacity, and blood coagulation measurement by ROTEM, TEG, or the like.

Since CTI is more expensive than aprotinin, an especially preferred embodiment includes one in which a blood collection tube is coated with low-molecular-weight heparin, and aprotinin and/or a small amount of CTI (not more than 25 μg/mL), and measurement is carried out by further adding a mixture of heparinase and CTI (for example, 10 to 50 μg/mL).

In cases where the blood is used only in a test mainly for blood coagulation, sodium citrate may be used instead of heparin. In such cases, blood may be collected using a blood collection tube containing sodium citrate (preferably about 11 mM) and a kallikrein inhibitor, and the measurement may be carried out by adding calcium (for example, calcium chloride; the same applies hereinafter), or calcium and CTI.

On the other hand, in cases where measurement is carried out using blood collected using a commonly available vacuum blood collection tube containing 3.2 to 3.8% sodium citrate, accurate measurement of the thrombogenic capacity is also possible by adding CTI (for example, 10 to 50 μg/mL), a kallikrein inhibitor (for example, 10 to 50 μg/mL aprotinin), and calcium upon the measurement since they suppress activation of contact factors and promotion of blood coagulation during the measurement. In such cases, even better suppression of blood coagulation is possible by addition, besides the CTI, kallikrein inhibitor, and calcium, of low-concentration (for example, not more than 0.5 unit (U)/mL) heparin, low-molecular-weight heparin, and/or danaparoid sodium (low-molecular-weight heparinoid containing heparan sulfate as a major component), so that the resulting blood is suitable for measurement of the mixed white thrombus formation capacity.

In cases where CTI, a kallikrein inhibitor, and calcium are added, preferably low-concentration heparin or heparan sulfate is further added, more preferably low-concentration tissue factor is further added, to a blood sample collected in a blood collection tube containing sodium citrate, to allow initiation of blood coagulation, analysis of more physiological blood coagulation reaction is possible in blood coagulation tests such as ROTEM and TEG.

In general, blood coagulation in the body cannot be simplified into extrinsic coagulation and intrinsic coagulation. It is said that a small amount of tissue factor expressed on the cell surface initiates blood coagulation, and then a small amount of thrombin produced causes activation of coagulation factors XI, VIII, and V, resulting in amplification of the blood coagulation (cell based coagulation model; Journal of Veterinary Emergency and Critical Care 19(1) 2009, pp 3 to 10). It is therefore thought that the above assay allows measurement of blood coagulation similar to that in the body since the blood coagulation is initiated by a small amount of tissue factor while suppressing activation of non-physiological blood coagulation caused by a rubber stopper. In recent years, coagulation factor VII (Novo-Seven), an inhibitor of the tissue factor pathway (TFPI: BAX499), and the like are used (or being developed) as hemostatic preparations, and the present invention may be useful also for evaluation of the effects of these agents.

Thus, blood subjected to anticoagulation treatment with heparin and a contact factor inhibitor can be used for measurement of both a platelet thrombus and a mixed white thrombus, and also for measurement of blood coagulation by ROTEM, TEG, or the like.

In cases where blood is collected with a commonly available blood collection tube containing 3.2 to 3.8% citric acid having a rubber stopper as a cap, measurement of a mixed white thrombus and measurement of blood coagulation are possible by adding calcium, an FXII inhibitor, a kallikrein inhibitor, and preferably, further adding a small amount of heparin or heparan sulfate upon the measurement.

The factor FXII inhibitor is preferably CTI, and the kallikrein inhibitor is preferably aprotinin. More preferably, a small amount of heparin or heparan sulfate is added together with CTI, aprotinin, and calcium chloride. By using this mixture, analysis of a mixed white thrombus in the presence of blood flow can be suitably carried out using a channel coated with tissue factor and collagen.

By further adding a small amount of tissue factor together with CTI, aprotinin, and heparin to allow initiation of blood coagulation, blood coagulation analysis using ROTEM, TEG, or the like can be suitably carried out.

In cases where these reagents are used, the small amount of tissue factor initiates blood coagulation in an environment in which activation of contact factors is inhibited by CTI, and then a small amount of thrombin produced causes feedback activation of coagulation factors XI, VIII, and V, resulting in amplification of the coagulation cascade, which then allows analysis of more physiological coagulation reaction.

The tissue factor to be used may be either tissue thromboplastin extracted from an animal tissue, or a soluble (extracellular domain) tissue factor prepared by genetic recombination technique. Examples of the recombinant tissue factor include Dade Innovin (Siemens) and HemosIL (IL Japan), which are commercially available as recombinant PT reagents.

The amount of tissue factor added is not limited. In cases where the amount of heparin or heparan sulfate added is large, a larger amount of tissue factor is required. For analysis of blood coagulation, initiation of blood coagulation preferably occurs after a period of 3 minutes to 30 minutes in normal blood. In cases where initiation of blood coagulation occurs within 3 minutes, extrinsic blood coagulation caused by the tissue factor has a large influence, and there is hardly contribution of intrinsic blood coagulation, so that diagnosis of hemophilia or the like cannot be suitably carried out in some cases. In cases where initiation of blood coagulation occurs after a period of more than 30 minutes, the test takes too much time.

In cases where a tissue factor prepared by genetic recombination is used, it is preferably added in an amount within the range of 0.1 nM to 10 nM.

In cases where heparin, and CTI or a kallikrein inhibitor are used for analysis of platelet thrombus formation in a blood sample from a patient, when the patient is receiving administration of heparin or low-molecular-weight heparin, the platelet thrombus formation capacity analyzed is affected thereby. In such cases, a reagent such as a heparinase-thrombin inhibitor (hirudin, argatroban, BAPA (benzylsulfonyl-D-Arg-Pro-4-amidinobenzylamide), or the like) may be added to degrade the low-molecular-weight heparin, thereby replacing it with the thrombin inhibitor. By this, the platelet thrombus formation capacity can be analyzed without being affected by the treatment of the patient with heparin.

The heparinase-thrombin inhibitor mixed reagent is useful also for analysis of the platelet thrombus formation capacity of blood collected with a widely commonly used blood collection tube coated with heparin.

In general, cardiac surgery using a cardiopulmonary support requires monitoring of reduction in hemostatic function due to blood dilution and recovery of hemostatic function with a hemostatic preparation (blood transfusion with a plasma derivative, platelet preparation, or the like). Basically, in patients who receive surgery, a blood collection route from an artery is secured through a catheter, and use of a vacuum blood collection tube is not required for such patients. In particular, when a cardiopulmonary support is used, a large amount of heparin is administered. Preferably, for a blood sample from such a patient, a mixed reagent of heparinase and a thrombin inhibitor (preferably a container preliminarily coated with the mixed reagent) is used in cases of analysis of a platelet thrombus (primary hemostatic capacity), and a mixed reagent of heparinase and CTI (preferably a container preliminarily coated with the mixed reagent) is used in cases of analysis of fibrin and a platelet thrombus (both primary hemostasis and secondary hemostasis). In cases where the container preliminarily coated with the reagent is used, the blood can be used for the measurement simply by adding the collected blood into the container and mixing it by inversion. In particular, in cases where a blood sample from a patient with an infection or blood from a patient with a remarkable decrease in the hematocrit due to blood loss or hemodilution is analyzed, disodium 4,4'-dinitrostilbene-2,2'-disulfonate (DNDS) may be added to the reagent to allow analysis of the thrombogenic capacity and hemostatic function while suppressing blood sedimentation. In such cases, the concentration of DNDS is preferably 20 to 200 µg/mL.

BRIEF DESCRIPTION OF THE DRAWINGS

FIG. 12A illustrates the results obtained without use of an anticoagulant in Example 9.

FIG. 12B illustrates the results obtained by addition of rivaroxaban at various concentrations in Example 9.

FIG. 12C illustrates the results of addition of dabigatran at various concentrations in Example 9.

EMBODIMENTS FOR CARRYING OUT THE INVENTION

The blood collection tube of the present invention comprises therein low-molecular-weight heparin or sodium citrate, and a contact factor inhibitor (an FXII inhibitor or a kallikrein inhibitor).

Heparin is a mucopolysaccharide having a molecular weight of about 5000 to 30,000 constituted by sulfated D-glucosamine, D-glucuronic acid, and L-iduronic acid forming a polymer. The heparin used in the present invention is preferably a low-molecular-weight heparin having a mass average molecular weight of 4500 to 6500. The heparin may also be a metal salt such as heparin sodium or heparin lithium. In general, heparin derived from bovine can be safely used, but, for example, those derived from an animal such as pig or dog, or those derived from human may also be used.

Examples of the FXII inhibitor include synthetic inhibitors such as CTI, COU254, and RD12. Among these, CTI is preferred. The CTI may be one disclosed in the following documents, may be a commercially available product, or may be one prepared from corn.

J Biol Chem. 1977 Nov. 25; 252(22): 8105-7.
Thromb Res. 1980 Oct. 15; 20(2): 149-62.
Blood. 1996 Nov. 1; 88(9): 3432-45.

COU254 and RD12 are described in, for example, the following documents.

Exp Transl Stroke Med. 2010; 2: 5. Published online 2010 Feb 15. doi: 10.1186/2040-7378-2-5

ACS Chem Biol. 2015 Aug. 21; 10(8): 1861-70. doi: 10.1021/acschembio.5b00103. Epub 2015 May. 19.

A Synthetic Factor XIIa Inhibitor Blocks Selectively Intrinsic Coagulation Initiation.

Baeriswyl V1, Calzavarini S2,3, Chen 51, Zorzi A1, Bologna L2,3, Angelillo-Scherrer A2,3, Heinis C1.

Examples of the kallikrein inhibitor include aprotinin. Other low-molecular-weight kallikrein inhibitors may also be used.

Expert Opin Investig Drugs. 2006 September; 15(9): 1077-90

Figure 1:
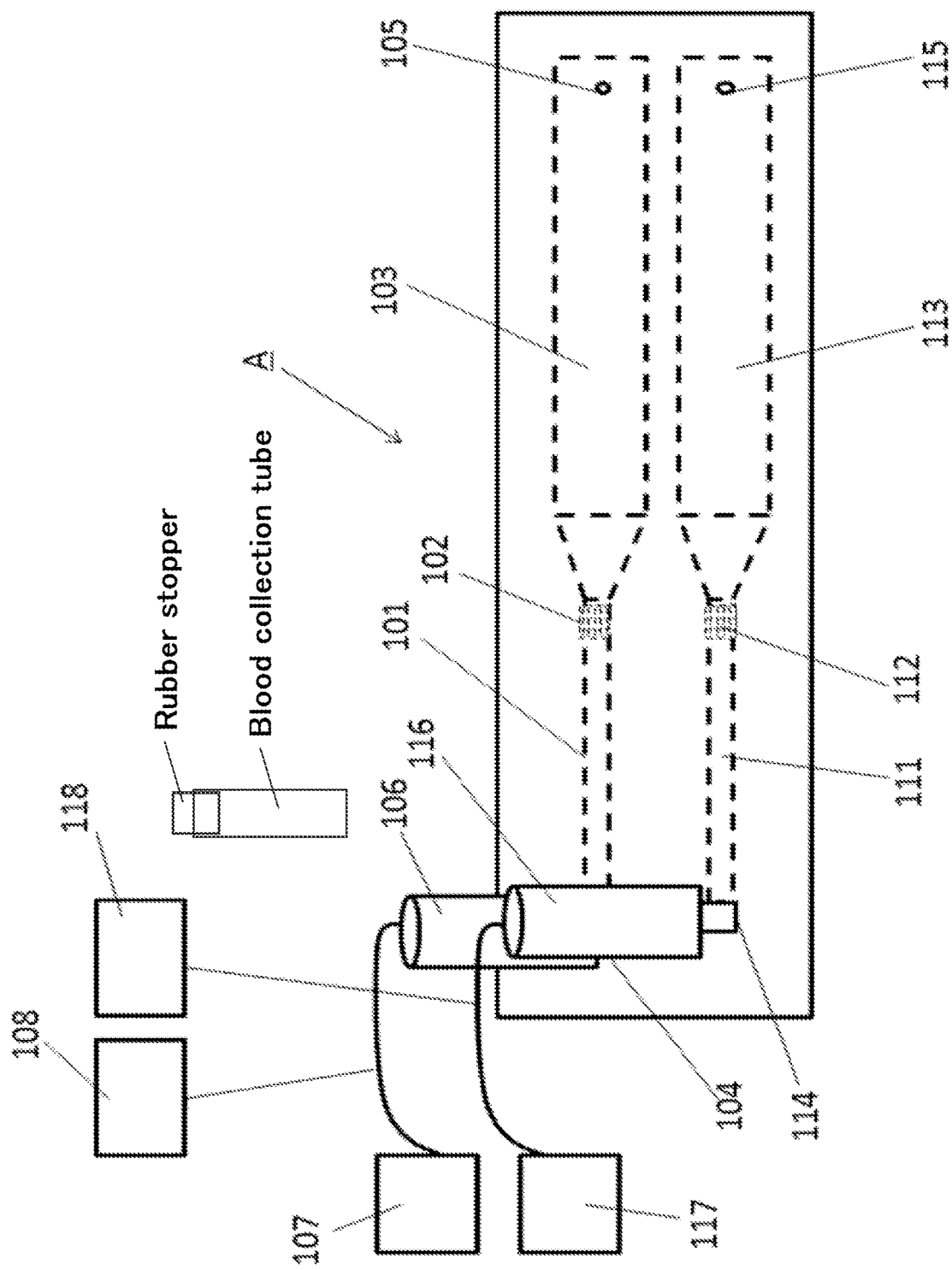
FIG. 1 is a diagram illustrating the first embodiment of the microchip for evaluation of the thrombogenic capacity using blood collected with the blood collection tube of the present invention.

The shape of the blood collection tube of the present invention is not limited, and may be the same shape as a known blood collection tube. In one exemplary embodiment of the present invention, as depicted in FIG. 1, the blood collection tube comprises a blood collection tube main body having a bottomed cylindrical shape, and a stopper body attached thereto for sealing the opening section of the blood collection tube main body.

The inside of the blood collection tube main body to which the stopper body is to be attached is preferably evacuated. The evacuation of the inside of the blood collection tube allows quick blood collection. The degree of evacuation may be appropriately set depending on the amount of blood to be collected.

Preferred examples of the bottomed tube in the blood collection tube of the present invention include glasses; homopolymers and copolymers of polyethylene terephthalate, polybutylene terephthalate, polyethylene naphthalate, polyethylene isophthalate, and/or the like; acrylic resins; polyethylenes; polypropylenes; polycarbonates; polyacetals; polyamides; and polyurethanes.

The stopper body for sealing of the opening section of the bottomed tube in the blood collection tube of the present invention is preferably a rubber, elastomer, or aluminum-deposited film. Examples of the rubber include chlorinated butyl rubber, brominated butyl rubber, isoprene rubber, and natural rubber. Examples of the elastomer include olefin-based, polyester-based, and polyurethane-based elastomers. Examples of the aluminum-deposited film include those having a shape in which a rubber button made of isoprene or the like is provided on the aluminum-deposited film to allow piercing with a needle, and the film is adhered to the bottomed tube.

Examples of the method for introducing heparin or sodium citrate, and a contact factor inhibitor such as an FXII inhibitor or a kallikrein inhibitor, into the blood collection tube include a method in which a solution of heparin or sodium citrate and the contact factor inhibitor is sprayed onto the inner wall of the blood collection tube, and then dried to allow their adhesion to the inner wall. By including heparin or sodium citrate and a contact factor inhibitor into a blood collection tube, sealing the opening end of the bottomed tube with a stopper body, and then sealing it with an aluminum-deposited film or a plastic wrapping material, protection against heat and moisture can be maintained for a longer period, and stability of the heparin or sodium citrate and the contact factor inhibitor can be increased. By performing silicone coating of the inner surface of the bottomed tube before allowing the heparin or sodium citrate and the contact factor inhibitor to be present in the blood collection tube of the present invention, abnormal coagulation/adhesion of blood, and the like can be prevented.

In the present invention, the low-molecular-weight heparin to be included in the blood collection tube as an anticoagulant is in an amount of preferably 1 to 10 units (anti-FXa units; international units) (1 to 10 IU/mL), more preferably 3 to 8 units (3 to 8 IU/mL) per 1 mL of the blood to be collected.

In the present invention, the sodium citrate to be included in the blood collection tube as an anticoagulant is preferably 3.2 to 3.8% sodium citrate in an amount of 1/10 volume with respect to the blood to be collected.

In the present invention, the amount of the FXII inhibitor to be included in the blood collection tube may be an amount in which blood coagulation factor XII can be inhibited. In a case of CTI, the amount is preferably 5 to 50 µg per 1 mL of the blood to be collected. The amount of CTI may also be an amount that is just enough for preventing activation of contact factors in the blood collection tube. The amount is, for example, not more than 25 µg/mL, preferably 5 to 20 µg/mL.

In the present invention, the amount of the kallikrein inhibitor to be included in the blood collection tube may be an amount in which kallikrein can be inhibited. In a case of aprotinin, the amount is preferably 1 to 50 µg per 1 mL of the blood to be collected. Both aprotinin and CTI may be included in the blood collection tube. In such a case, the amount of CTI may be an amount that is enough for preventing activation of contact factors in the blood collection tube, for example, 1 to 10 µg/mL.

Blood collected using such a blood collection tube is used for analysis of the thrombogenic capacity. The method for analyzing the thrombogenic capacity is not limited as long as it is an in vitro method. In a preferred method, the thrombogenic capacity is analyzed in the presence of blood flow using a microchip provided with a microchannel(s) mimicking a blood vessel(s) therein. The blood may also be used for conventional coagulation analysis such as ROTEM or TEG.

As methods for analyzing the thrombogenic capacity using such a microchip, the present inventors have reported a microchip for analysis of a platelet thrombus having a channel-dividing section in the middle of a channel(s), and a microchip for analysis of a mixed white thrombus having a thrombus monitoring section coated with collagen and tissue factor in the middle of a channel(s).

First, a method for analyzing the platelet thrombus formation capacity using a microchip A for analysis of a platelet thrombus is described below with reference to FIG. 1. In the example illustrated in FIG. 1, two channels are provided in parallel. However, this is merely an example, and, of course, the microchip may have a single channel, or may be in a different mode.

Reservoirs (blood storage containers) 106 and 116 are connected in an inverted position to a first inlet 104 and a second inlet 114, respectively, of the microchip A, and liquid transfer pumps 107, and 117 are connected to the reservoirs 106 and 116. To the liquid transfer pumps 107 and 117, pressure sensors 108 and 118 are connected.

Immediately before the measurement, blood collected with the blood collection tube of the present invention is introduced into the reservoirs 106 and 116, and then the measurement is carried out.

As the liquid for the liquid transfer pumps 107 and 117, a liquid having a specific gravity lower than that of blood, such as mineral oil or physiological saline is used. This liquid is introduced using the liquid transfer pumps 107 and 117 into the reservoirs 106 and 116, respectively, in which blood is preliminarily filled, thereby overlaying the liquid on the blood. The liquid is then pushed using the pumps 107 and 117 to introduce the blood into the channels 101 and 111. By measuring the inflow pressure of the liquid, the inflow pressure of the blood into each channel can be indirectly measured.

More specifically, mineral oil is injected from the liquid transfer pumps 107 and 117 into the reservoirs 106 and 116. By this, the mineral oil is overlaid on the blood, and the blood is pushed into the channels 101 and 111 of the microchip 1. The blood passes through the channels 101 and 111, and then reaches the reaction sections 102 and 112. Each of the first reaction section and the second reaction section is coated with collagen, and provided with a plurality of channel-dividing walls such as the ones disclosed in Patent Documents 2 and 3, such that the walls are present along the direction of blood flow to divide the width of each channel into a plurality of segments, thereby allowing occlusion by thrombus formation to occur more quickly in the dividing wall portion than in other portions. The intervals between the channel-dividing walls are preferably not more than 200 µm. In the channel-dividing section, the width of the channel is preferably divided into not less than five segments by the channel-dividing walls. The shape of the channel-dividing walls is not limited as long as the width of the channel can be divided into a plurality of segments. As described in Patent Document 3, the channel-dividing walls may be treated such that surface roughness (Ra) is 10 to 200 nm.

Thrombus formation by platelets occurs when the blood passes through the reaction sections, and increases in the inflow pressure due to this thrombus formation can be observed. By detecting the patterns of these pressure increases using the pressure sensors, and comparing the detected patterns, blood properties, that is, the platelet thrombus formation capacity, can be evaluated.

The blood subjected to the test reaches waste liquid storage sections 103 and 113 from the ends of the channels 101 and 111, and is then stored therein, followed by being discharged from waste liquid outlets 105 and 115. In cases where a blood absorbent material such as a sponge impregnated with EDTA or the like is placed in each waste liquid storage section, the blood waste does not adversely affect the pressure measurement since it is absorbed into the blood absorbent material and not coagulated.

Figure 2:
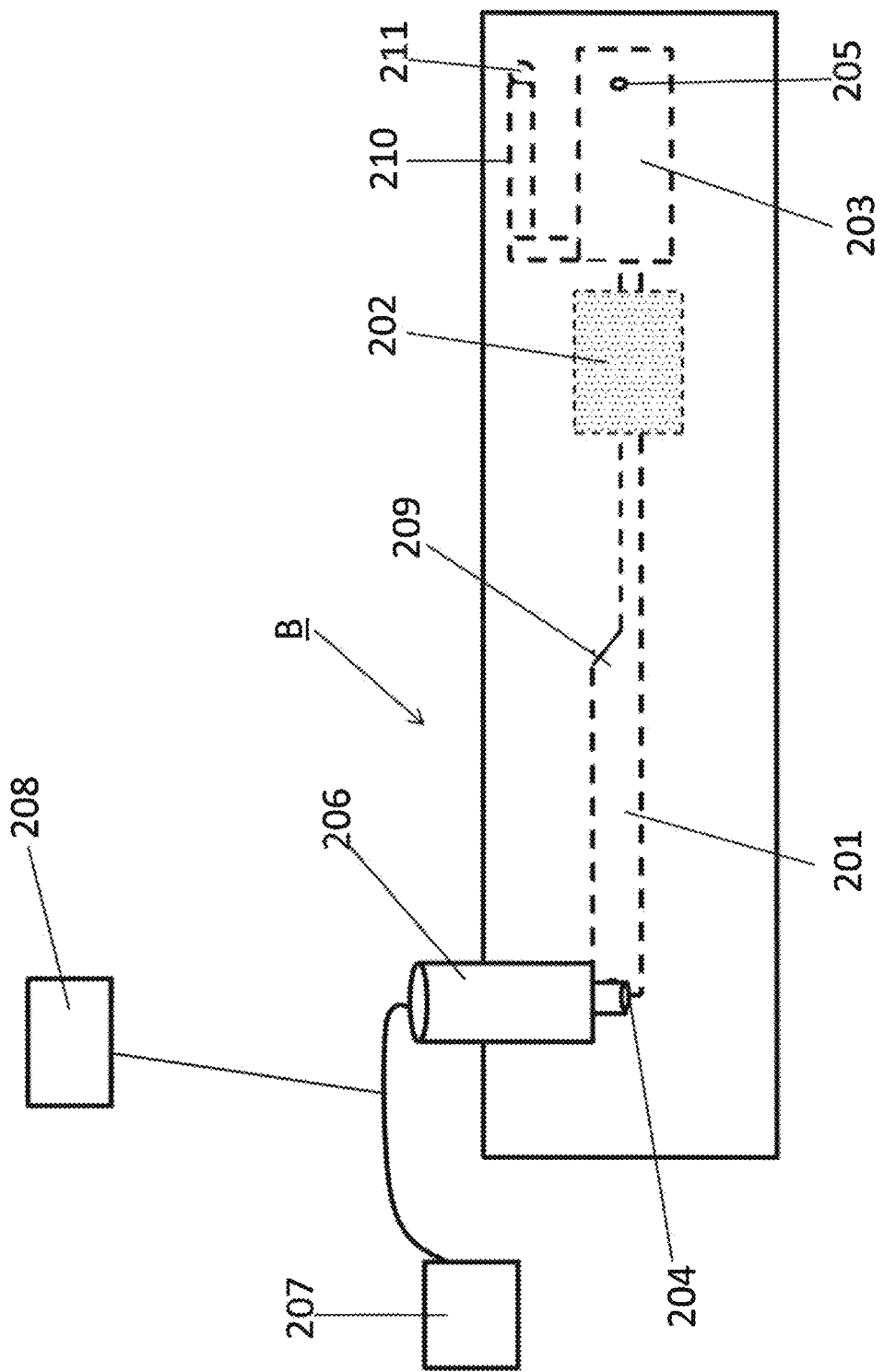
FIG. 2 is a diagram illustrating the second embodiment of the microchip for evaluation of the thrombogenic capacity using blood collected with the blood collection tube of the present invention.

A method for analyzing the mixed white thrombus formation capacity using a microchip B for analysis of a mixed white thrombus is described below with reference to FIG. 2. The example illustrated in FIG. 2 is a mode in which a blood coagulation inhibitor is added to blood that has passed through a channel. However, this is merely an example, and the microchip may be, of course, in a different mode.

A reservoir (blood storage container) 206 is connected in an inverted position to an inlet 204 of the microchip B, and a liquid transfer pump 207 is connected to the reservoir 206. To the liquid transfer pump 207, a pressure sensor 208 is connected.

Immediately before the measurement, heparinase is added to blood collected with the blood collection tube of the present invention to degrade heparin. The blood is then introduced into the reservoir 206, and the measurement is carried out. Depending on the amount of heparin in the blood sample collected, the amount of heparinase is preferably 0.1 to 10 units (0.1 to 10 IU/mL), more preferably 0.2 to 5 units (0.2 to 5 IU/mL) per 1 mL of the blood.

In cases where the amount of CTI to be present in the blood collection tube is an amount that is just enough for preventing activation of contact factors in the blood collection tube, addition of additional CTI together with the heparinase is preferred for mixed white thrombus analysis. Preferably, for example, the blood collection tube contains CTI in an amount of not more than 25 µg/mL (for example, 5 to 20 µg/mL) therein, and not less than 10 µg/mL CTI is added thereto together with heparinase immediately before the measurement, followed by subjecting the resulting mixture to mixed white thrombus analysis.

As the liquid for a liquid transfer pump 207, a liquid having a specific gravity lower than that of blood, such as mineral oil or physiological saline is used. This liquid is introduced using the liquid transfer pump 207 into a reservoir 206 in which blood is preliminarily filled, thereby overlaying the liquid on the blood. The liquid is then pushed using the pump 207 to introduce the blood into a channel 201. By measuring the inflow pressure of the liquid, the inflow pressure of the blood into the channel can be indirectly measured.

More specifically, mineral oil is injected from the liquid transfer pump 207 into the reservoir 206. By this, the mineral oil is overlaid on the blood, and the blood is pushed into the channel 201 of the microchip B. The blood passes through a narrow section 209 provided in the middle of the channel, and then reaches a reaction section 202. By providing the narrow section, high-shear-stress-induced platelet aggregation can be monitored, and thrombus formation in atherothrombosis can be reproduced, which is preferred. Since the reaction section is coated with collagen and tissue factor, thrombus formation occurs in this section. The inclusion of collagen and tissue factor comprehensively induces phenomena involved in thrombus formation, such as adhesion and aggregation of platelets on the collagen and activation of the coagulation system caused by the tissue factor. An increase in the inflow pressure due to this thrombus formation can be observed. By detecting the pattern of the pressure increase using the pressure sensor, and comparing the detected pattern, blood properties, that is, the mixed white thrombus formation capacity, can be evaluated.

The blood subjected to the test reaches a waste liquid storage section 203 from the end of the channel 201. Subsequently, the blood is mixed with a blood coagulation inhibitor injected from a blood coagulation inhibitor inlet 211 through a blood coagulation inhibitor channel 210, and then discharged from an outlet 205. The blood coagulation inhibitor is used for the purpose of preventing clogging or a pressure increase due to blood coagulation of the waste liquid. The blood coagulation inhibitor may be a chelating agent such as EDTA or citric acid; an acid or alkaline solution; an alcohol; or a denaturant such as guanidine, urea, or SDS.

In cases where mixed white thrombus formation is analyzed using a commonly used blood collection tube containing sodium citrate, the measurement can be suitably carried out by initiating the coagulation reaction by addition of calcium (preferably calcium chloride) and a contact factor inhibitor(s) (factor FXII inhibitor and/or kallikrein inhibitor).

The amount of sodium citrate contained in a commonly used blood collection tube is adjusted such that its concentration becomes 0.32 to 0.38% in blood.

The concentration of calcium chloride added is not limited as long as the chelating action of sodium citrate can be canceled, and is preferably 11 to 12 mM.

Examples of the contact factor inhibitor include FXII inhibitors and kallikrein inhibitors.

The FXII inhibitor is not limited as long as it is a substance having FXII-inhibitory activity. CTI may be used as the FXII inhibitor. In cases of CTI, it is used in an amount of preferably 5 to 200 µg, more preferably 10 to 50 µg per 1 mL of blood.

The kallikrein inhibitor is not limited, and preferably aprotinin. In cases of aprotinin, it is used in an amount of preferably 1 to 100 µg per 1 mL of blood.

By using an FXII inhibitor and a kallikrein inhibitor in combination, more complete inhibition of activation of contact factors is possible, which is preferred.

In particular, aprotinin inhibits not only kallikrein, but also plasmin. Plasmin has a relatively low substrate specificity, and activates blood coagulation factors.

Thus, while completely suppressing activation of contact factors by inhibition of kallikrein, activation of blood coagulation factors through non-specific pathways can be more completely suppressed by inhibition of plasmin. In cases where plasmin is suppressed, fibrinolytic response is suppressed, which is preferred for diagnosis of blood coagulation conditions, for example, hemophilia, of a patient, or for evaluation of an anticoagulant.

When analysis of a mixed white thrombus is carried out, in cases where heparin, low-molecular-weight heparin, and/or heparan sulfate (for example, danaparoid sodium) is/are added in a small amount in which formation of the mixed white thrombus is not affected, blood coagulation due to contact with the container can be completely suppressed, which is preferred.

The amount is preferably about 0.01 to 0.2 U/mL in cases of heparin, about 0.01 to 0.5 IU/mL in cases of low-molecular-weight heparin, and about 0.01 to 0.5 U (anti-FXa unit)/mL in cases of danaparoid sodium.

When the blood is allowed to flow through a microchip coated with collagen and tissue factor, activation (adhesion/aggregation reaction) of platelets and activation of extrinsic coagulation due to the tissue factor coating occur at the same time, and then intrinsic coagulation is promoted on the activated platelet surface on the collagen in the microchannel, leading to formation of a mixed white thrombus in the presence of blood flow.

In cases where blood coagulation is analyzed using a commonly used blood collection tube containing sodium citrate, analysis of more physiological blood coagulation reaction can be carried out by initiating the blood coagulation by addition of a small amount of tissue factor as well as calcium chloride, the contact factor inhibitor, and a small amount of heparin (or low-molecular-weight heparin or heparan sulfate).

In such cases, the tissue factor initiates extrinsic blood coagulation in a state where blood coagulation due to the blood collection tube or the measurement container is completely suppressed by the calcium chloride, contact factor inhibitor, and small amount of heparin (or low-molecular-weight heparin or heparan sulfate), and then a small amount of thrombin produced initiates intrinsic blood coagulation, resulting in amplification of the blood coagulation reaction.

The concentration of the tissue factor used is not limited, and is preferably 100 nM to 0.1 nM in cases of a recombinant soluble tissue factor. In cases where the amount of heparin added is large, a larger amount of tissue factor needs to be added. The measurement can be easily carried out in cases where initiation of blood coagulation occurs after a period of 3 minutes to 30 minutes when blood from a healthy individual is used.

The blood coagulation analysis device used is not limited, and preferably an analysis device for blood coagulation in the absence of blood flow such as ROTEM, TEG, or Sonoclot.

Accordingly, the present invention provides a reagent for analyzing the thrombogenic capacity or the blood coagulation capacity, the reagent comprising calcium, a blood coagulation factor XII (FXII) inhibitor, and a kallikrein inhibitor. The analysis reagent preferably further contains heparin or heparan sulfate, more preferably further contains tissue factor. The analysis reagent may be provided as a reagent kit separately including these components.

EXAMPLES

Example 1

Blood was collected in a blood collection tube A (having a butyl rubber stopper; containing 3.2% sodium citrate; manufactured by Sunphoria Co., Ltd.) or a blood collection tube B (sealed with a film seal, without use of a rubber stopper; containing 3.2% sodium citrate; manufactured by Terumo Corporation), and ROTEM measurement was carried out.

The reaction was initiated using the following different reagents.

(1) STARTEM (trademark) reagent (calcium chloride; final concentration, 12 mM) was added to the blood in the blood collection tube A.

(2) CTI (final concentration, 50 μg/mL) and calcium chloride (final concentration, 12 mM) were added to the blood in the blood collection tube A.

(3) Aprotinin (final concentration, 10 μg/mL) was added to the blood collection tube A before the blood collection, and then the blood collection was carried out, followed by addition of CTI (final concentration, 50 μg/mL) and calcium chloride (final concentration, 12 mM).

(4) Aprotinin (final concentration, 10 μg/mL) and CTI (final concentration, 10 μg/mL) were added to the blood collection tube A before the blood collection, and then the blood collection was carried out, followed by addition of STARTEM reagent (calcium chloride; final concentration, 12 mM).

(5) Aprotinin (final concentration, 10 μg/mL) and CTI (final concentration, 10 μg/mL) were added to the blood collection tube A before the blood collection, and then the blood collection was carried out, followed by addition of CTI (final concentration, 50 μg/mL) and STARTEM reagent (calcium chloride; final concentration, 12 mM).

(6) STARTEM reagent (calcium chloride; final concentration, 12 mM) was added to the blood in the blood collection tube B.

(7) CTI (final concentration, 50 μg/mL) and calcium chloride (final concentration, 12 mM) were added to the blood in the blood collection tube B.

Figure 3:
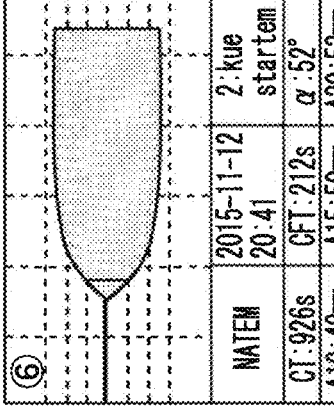
FIG. 3 is a diagram illustrating the results of ROTEM measurement that was carried out by adding calcium chloride or both calcium chloride and CTI to blood collected using each blood collection tube containing sodium citrate; Example 1.

The results are shown in FIG. 3.

By the addition of calcium chloride, the blood collection tube with a butyl rubber stopper caused coagulation of the collected blood more quickly than the blood collection tube with a film seal. Moreover, while the addition of CTI suppressed the calcium chloride-induced blood coagulation of the blood in the blood collection tube with a film seal, the suppression of the calcium chloride-induced blood coagulation by the addition of CTI was limited in the blood collection tube with a butyl rubber stopper. However, in the case where calcium chloride was added to the blood collected in the blood collection tube with a butyl rubber stopper in which aprotinin and a relatively low concentration of CTI were added, blood coagulation was remarkably suppressed. In the case where blood coagulation was initiated by addition the mixture of calcium chloride and CTI, even stronger suppression of blood coagulation occurred. Blood coagulation could be best suppressed in the case where aprotinin and a low concentration of CTI were preliminarily added, and then blood collection was carried out, followed by adding CTI again upon the measurement.

Example 2

ROTEM analysis was carried out using blood collected in a blood collection tube C (having a butyl rubber stopper; containing 2 IU/mL low-molecular-weight heparin; manufactured by Sunphoria) (sample A), blood collected in a blood collection tube C to which aprotinin (final concentration, 10 μg/mL) was added before the blood collection (sample B), and blood collected in a blood collection tube C to which aprotinin (final concentration, 10 μg/mL) and CTI (final concentration, 10 μg/mL) were added before the blood collection (sample C). The reaction was initiated using the following reagents.

(1) Heparinase (final concentration, 0.17 IU/mL) was added to sample A.

(2) Heparinase (final concentration, 0.17 IU/mL) and CTI (final concentration, 50 μg/mL) were added to sample B.

(3) Heparinase (final concentration, 0.17 IU/mL) and CTI (final concentration, 50 μg/mL) were added to sample B.

Figure 4:
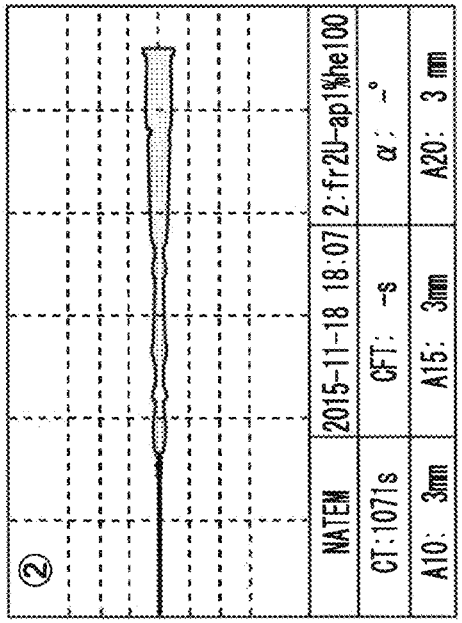
FIG. 4 is a diagram illustrating the results of ROTEM measurement that was carried out by adding heparinase or both heparinase and CTI to blood collected using a blood collection tube containing low-molecular-weight heparin; Example 2.
Figure 4:
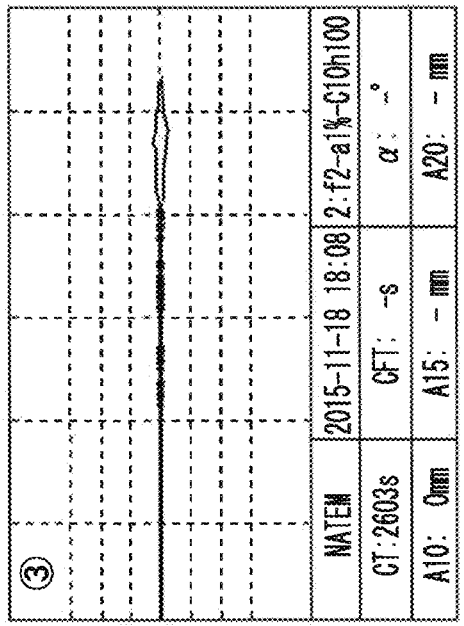
Figure 4:
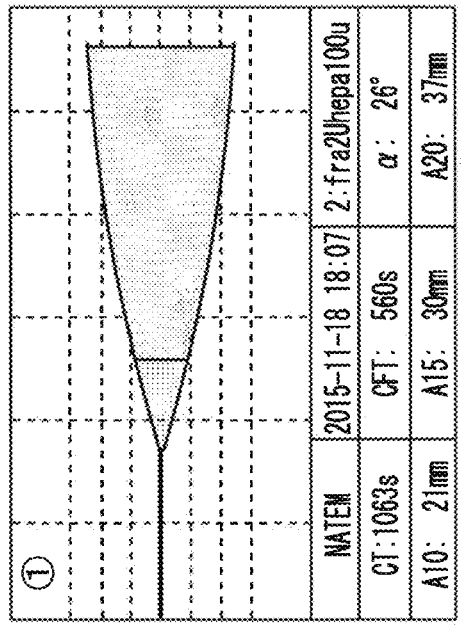

The results are shown in FIG. 4.

When blood was collected in the blood collection tube having a rubber stopper and containing low-molecular-weight heparin, initiation of blood coagulation occurred quickly after addition of heparinase. When 50 μg/mL CTI in addition to heparinase was added upon the start of the measurement in the case of (1), no suppression of blood coagulation occurred.

In contrast, when low-molecular-weight heparin, aprotinin, and CTI were preliminarily added, and then blood collection was carried out, followed by addition of heparinase and CTI upon the start of the measurement, remarkable suppression of blood coagulation occurred.

Example 3

Calcium chloride (final concentration, 12 mM) and CTI (final concentration, 50 μg/mL) were added to blood collected in a blood collection tube A, and to blood collected in a blood collection tube A to which aprotinin (final concentration, 10 µg/mL) was added before the blood collection. The thrombogenic capacity was analyzed using the device of FIG. 2. The analysis was carried out at a flow rate of 10 µL/min.

Figure 5:
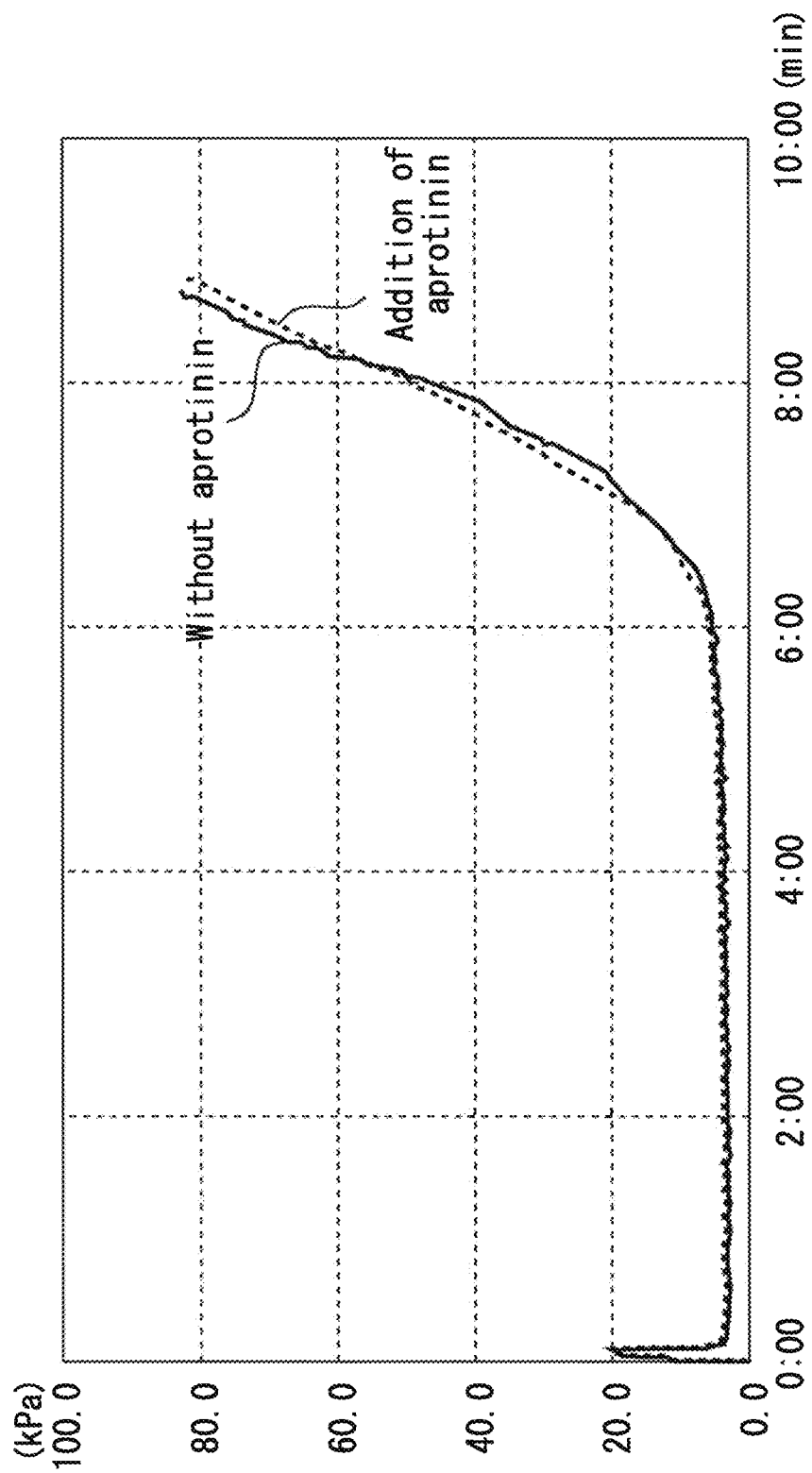
FIG. 5 is a diagram illustrating the results of measurement of white thrombus formation that was carried out by adding calcium chloride and CTI to blood collected using each blood collection tube containing sodium citrate; Example 3.

The results are shown in FIG. 5.

The addition of aprotinin in addition to citric acid before the blood collection did not influence the data in evaluation of the thrombogenic capacity in the presence of blood flow. However, it is considered, according to the results in Example 1, that blood coagulation (clot formation) in the absence of blood flow in the reservoir is suppressed, so that addition of aprotinin enables evaluation of white thrombus formation in the absence of blood flow while suppressing blood coagulation in the reservoir.

Reference Example

Calcium chloride (final concentration, 12 mM) and CTI (final concentration, 50 µg/mL) were added to blood collected in a blood collection tube B, and heparinase (final concentration, 0.17 IU/mL) was added to blood collected in a blood collection tube C, followed by performing analysis of the thrombogenic capacity using the device of FIG. 2.

Figure 6:
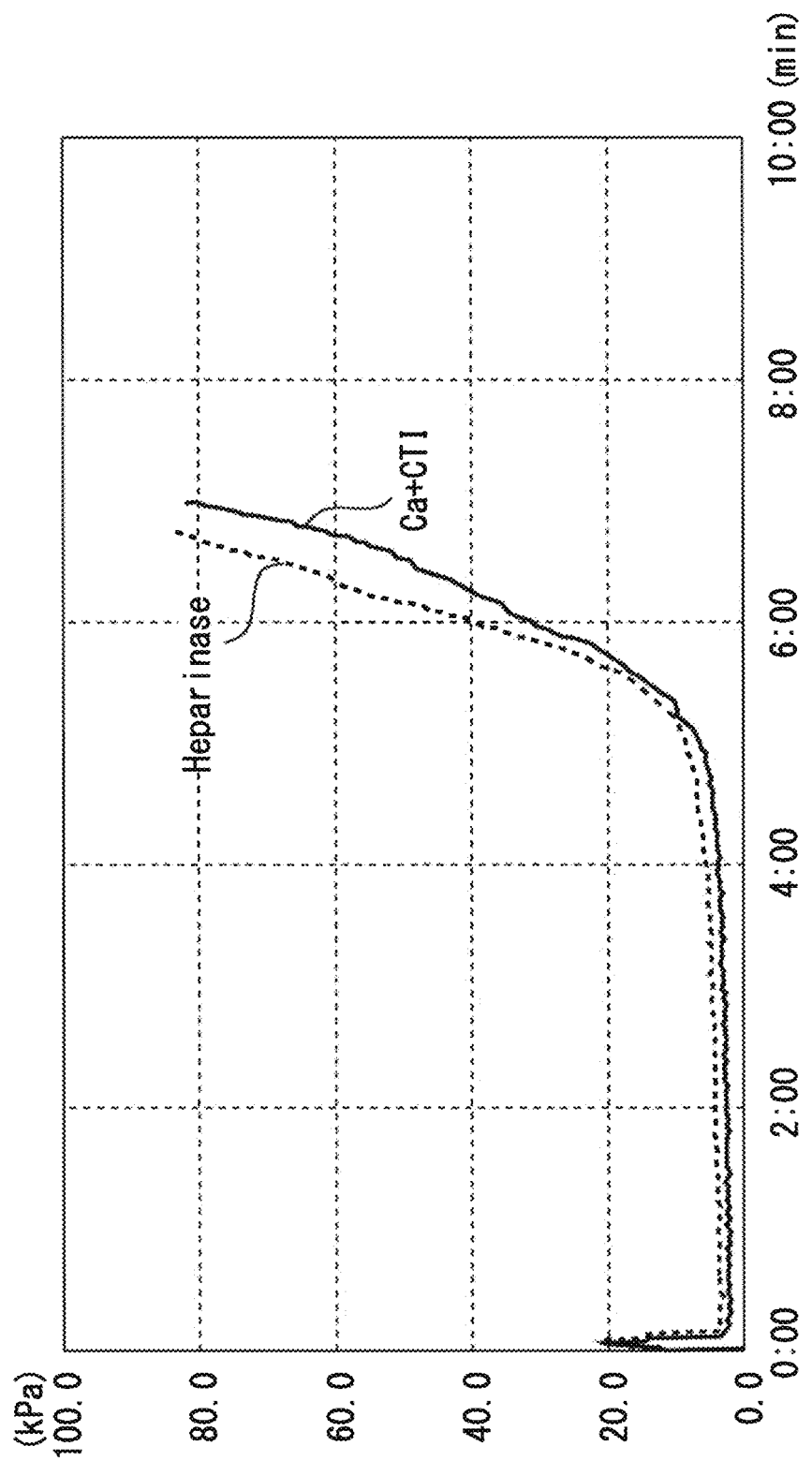
FIG. 6 is a diagram illustrating the results of measurement of white thrombus formation that was carried out by adding calcium chloride and CTI to blood collected using each blood collection tube containing sodium citrate, and the results of measurement of white thrombus formation that was carried out by adding heparinase to blood collected using each blood collection tube containing low-molecular-weight heparin; Reference Example.

The results are shown in FIG. 6.

Similarly to the case where calcium chloride and CTI were added to citric acid-treated blood, analysis of the thrombogenic capacity was possible when heparinase was added to the blood collection tube (containing low-molecular-weight heparin and CTI) having a rubber stopper, and the measurement was carried out therewith.

Example 4

Blood collected in a vacuum blood collection tube containing low-molecular-weight heparin (final concentration, 2 IU/mL) and CTI (final concentration, 50 µg/mL), in a hirudin blood collection tube (manufactured by Roche Diagnostic; hirudin final concentration, 50 µg/mL), or in a BAPA blood collection tube (BAPA final concentration, 100 µM) was used to measure platelet thrombus formation using the device shown in FIG. 1.

In every case, a vacuum blood collection tube having a butyl rubber stopper was used.

Figure 7:
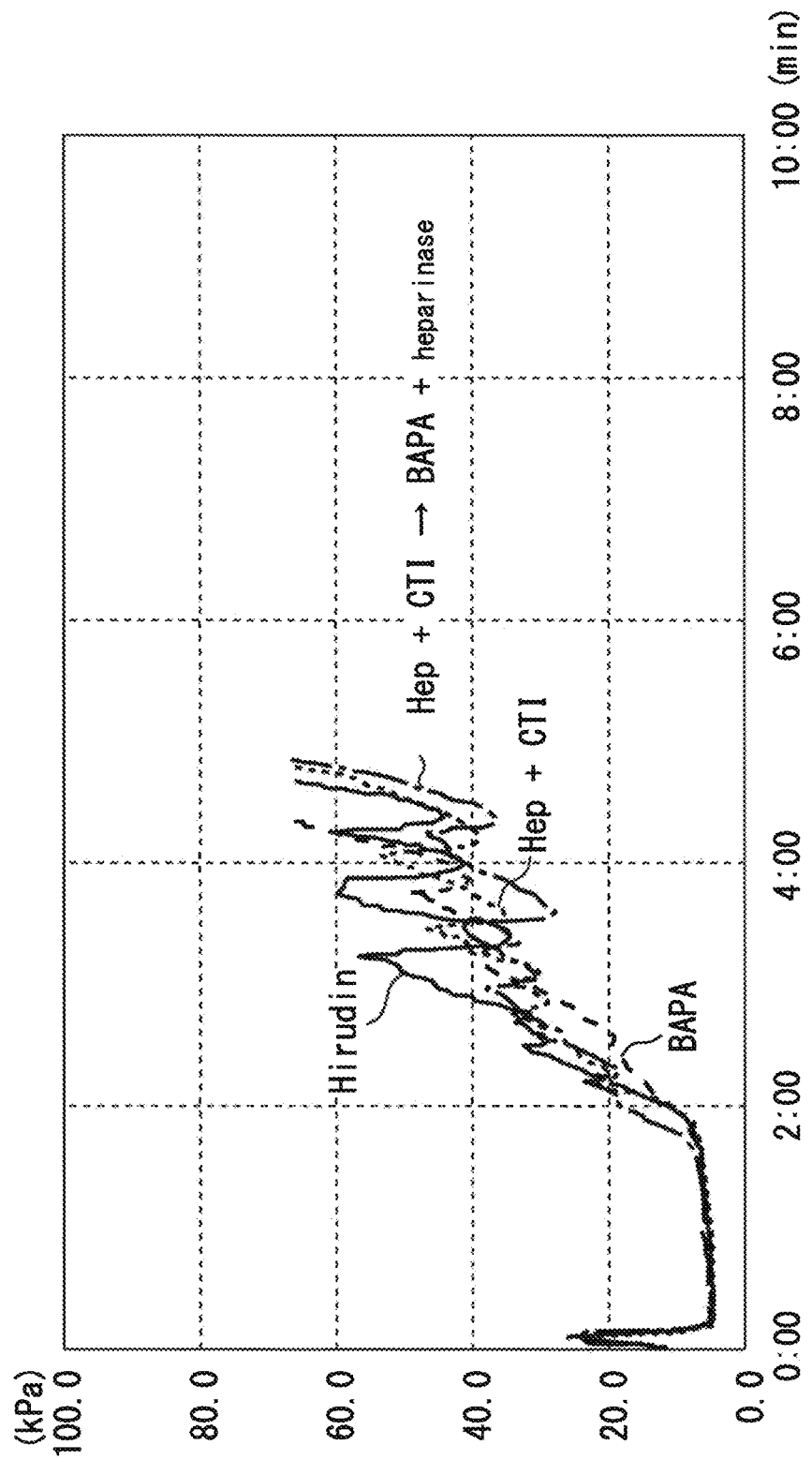
FIG. 7 is a diagram illustrating the results of measurement of platelet thrombus formation that was carried out using blood collected in a vacuum blood collection tube containing low-molecular-weight heparin and CTI, in a hirudin blood collection tube, or in a BAPA blood collection tube; Example 4.

As a result, as shown in FIG. 7, the blood in each blood collection tube similarly allowed analysis of platelet thrombus formation. Also in a case where heparinase and BAPA reagent (final concentrations, 0.17 IU/mL and 100 µM, respectively) were added to the blood in the blood collection tube containing low-molecular-weight heparin and CTI 30 minutes after the blood collection, measurement of platelet thrombus formation was possible.

Example 5

Blood was collected in a heparin blood collection tube manufactured by BD, and, 30 minutes later, a heparinase-BAPA mixed reagent was added to the blood such that their final concentrations were 0.17 IU/mL and 100 µM, respectively, to provide a blood sample.

For comparison, a blood sample collected in a hirudin blood collection tube (Roche Diagnostic) was used.

Using these blood samples, flow measurement of platelet thrombus formation was carried out using the device shown in FIG. 1. Blood was carried out at 18 µL/min.

In every case, a vacuum blood collection tube having a butyl rubber stopper was used.

Figure 8:
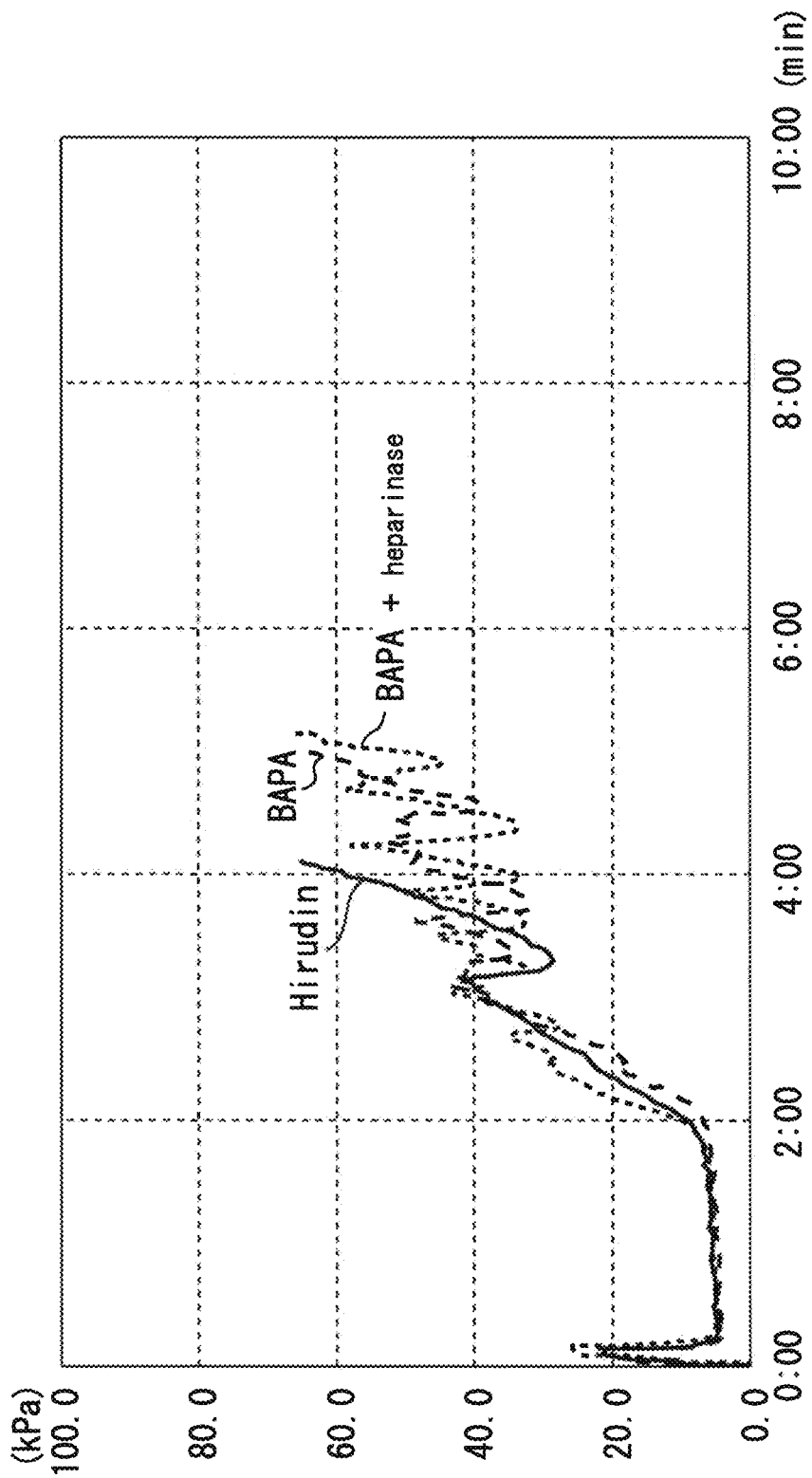
FIG. 8 is a diagram illustrating the results of measurement of platelet thrombus formation that was carried out by adding a heparinase-BAPA mixed reagent to blood collected in a heparin blood collection tube manufactured by BD; Example 5.

The results are shown in FIG. 8.

By the addition of the heparinase-BAPA mixed reagent to the blood collected in the heparin blood collection tube, analysis of platelet thrombus formation was possible similarly to the case where blood was collected using the hirudin blood collection tube.

In contrast, when the blood collected in the heparin blood collection tube was directly subjected to similar measurement, a pressure increase due to platelet thrombus formation was hardly observed.

Example 6

To a blood sample collected in a sodium citrate blood collection tube manufactured by BD (containing 3.2% sodium citrate in an amount of 1/10 volume with respect to the blood), the following reagents were added to perform ROTEM measurement.

(1) STARTEM reagent
(2) Calcium chloride (final concentration, 12 mM) and CTI (final concentration, 50 µg/mL)
(3) Calcium chloride (final concentration, 12 mM), CTI (final concentration, 50 µg/mL), and aprotinin (final concentration, 20 µg/mL)
(4) Calcium chloride (final concentration, 12 mM), CTI (final concentration, 50 µg/mL), aprotinin (final concentration, 20 µg/mL), and danaparoid sodium (final concentration, 0.25 U/mL)

Figure 9:
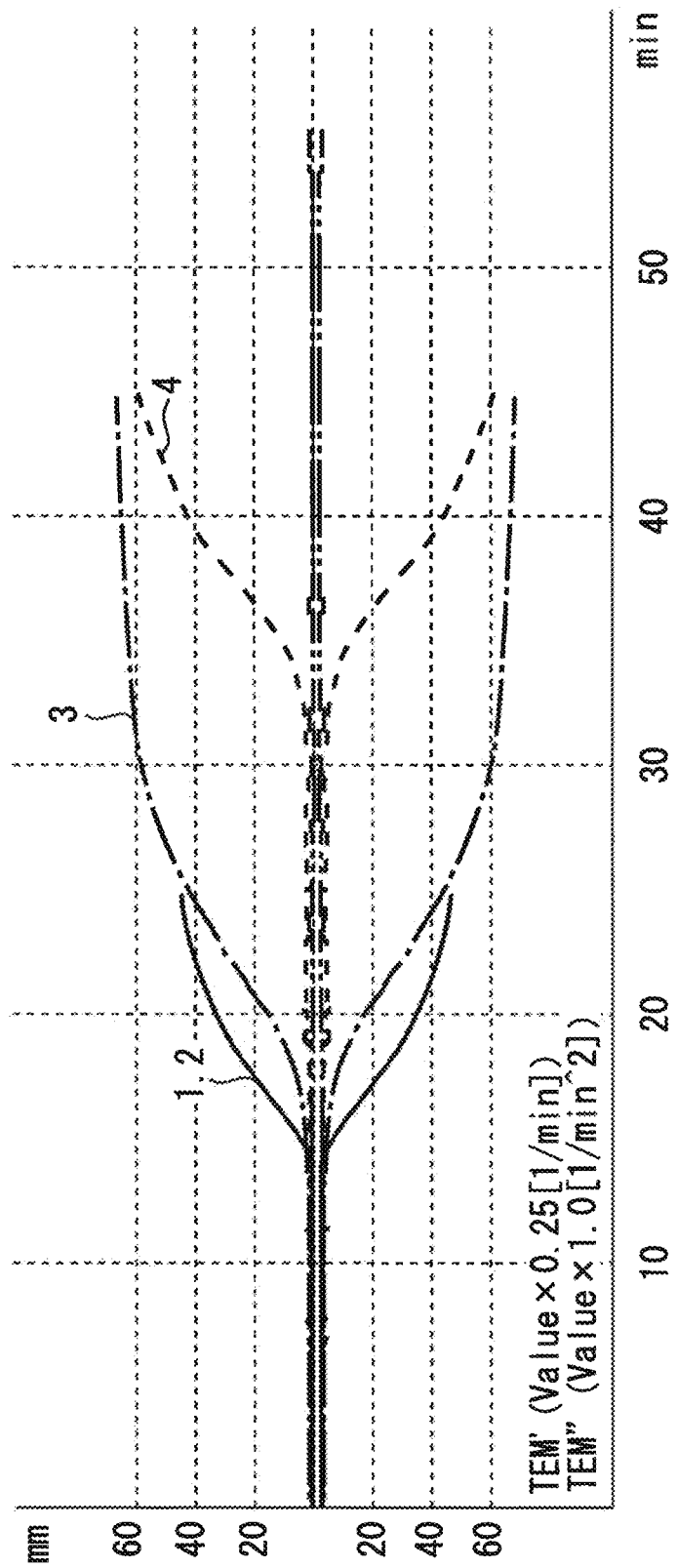
FIG. 9 is a diagram illustrating the results of ROTEM measurement that was carried out by adding each reagent to blood collected in a sodium citrate blood collection tube manufactured by BD; Example 6.

The results are shown in FIG. 9.

The results for (1), (2), (3), and (4) are shown from the left in this order (in the order of initiation of coagulation).

Addition of aprotinin together with calcium chloride and CTI suppressed initiation of coagulation, and further addition of a low concentration of danaparoid sodium resulted in complete suppression of blood coagulation.

Also by addition of (3) or (4), similar results were obtained for formation of a mixed white thrombus in a microchip coated with tissue factor and collagen.

Example 7

To a blood sample collected in a sodium citrate blood collection tube manufactured by BD (containing 3.2% sodium citrate in an amount of 1/10 volume with respect to the blood), the following reagents were added to perform ROTEM measurement.

(1) STARTEM reagent (calcium chloride reagent)
(2) Calcium chloride (final concentration, 12 mM) and CTI (final concentration, 50 µg/mL)
(3) Calcium chloride (final concentration, 12 mM), CTI (final concentration, 50 µg/mL), and aprotinin (final concentration, 20 µg/mL)
(4) Calcium chloride (final concentration, 12 mM), CTI (final concentration, 50 µg/mL), aprotinin (final concentration, 20 µg/mL), and heparin sodium (Mochida Pharmaceutical Co., Ltd.; final concentration, 0.15 U/mL)

Figure 10:
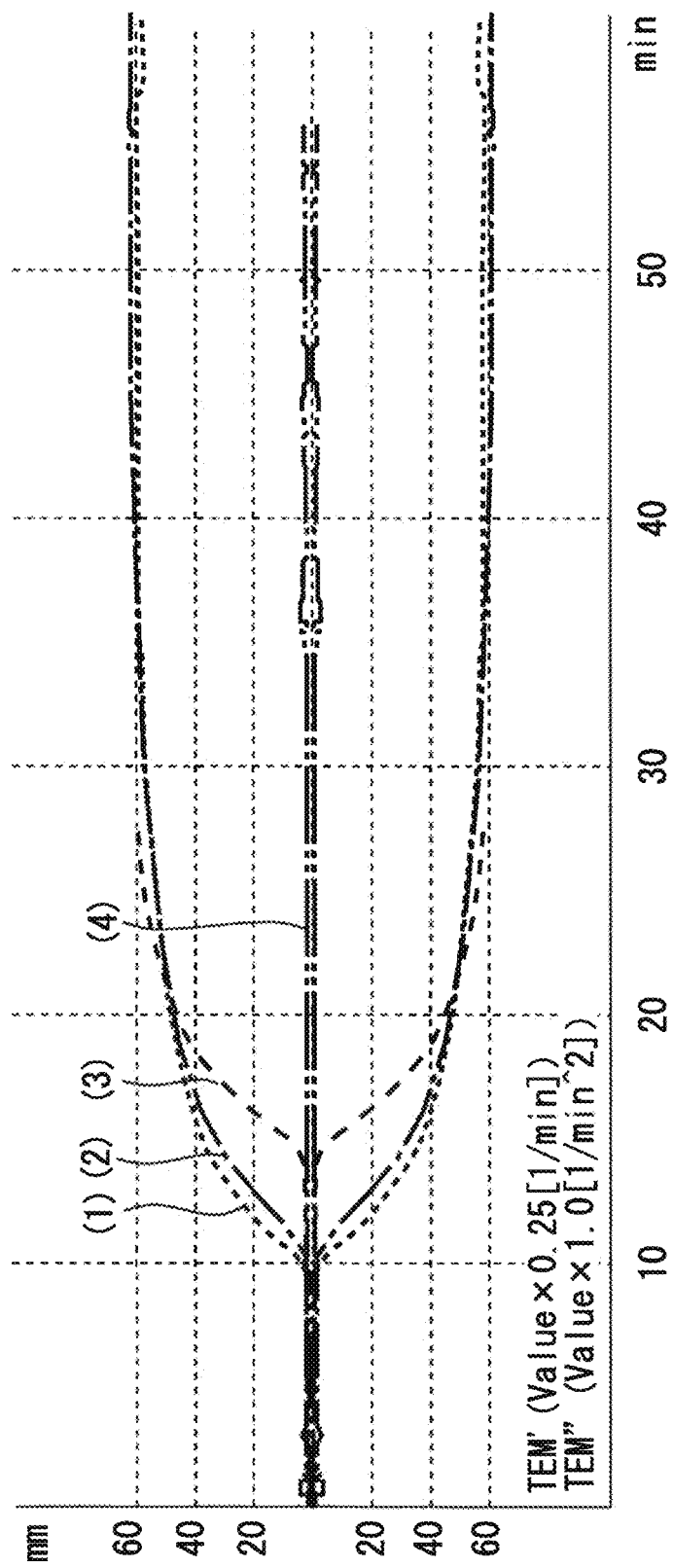
FIG. 10 is a diagram illustrating the results of ROTEM measurement that was carried out by adding each reagent to blood collected in a sodium citrate blood collection tube manufactured by BD; Example 7.

The results are shown in FIG. 10.

The results for (1), (2), (3), and (4) are shown from the left in this order (in the order of initiation of coagulation).

Addition of aprotinin together with calcium chloride and CTI suppressed initiation of blood coagulation, and further addition of a low concentration of heparin sodium resulted in complete suppression of blood coagulation.

Example 8

A blood sample prepared by adding calcium chloride (final concentration, 12 mM) and CTI (final concentration, 50 µg/mL) to blood collected in a blood collection tube B (sealed with a film seal, without use of a rubber stopper; containing 3.2% sodium citrate; manufactured by Terumo Corporation) and a blood sample prepared by adding calcium chloride (final concentration, 12 mM), CTI (final concentration, 50 µg/mL), aprotinin (final concentration, 20 µg/mL), and heparin sodium (final concentration, 0.15 U/mL) to blood collected in a sodium citrate blood collection tube manufactured by BD (containing 3.2% sodium citrate in an amount of 1/10 volume with respect to the blood) were used to perform analysis of the thrombogenic capacity using the device of FIG. 2. The analysis was carried out at a flow rate of 10 µL/min.

Figure 11:
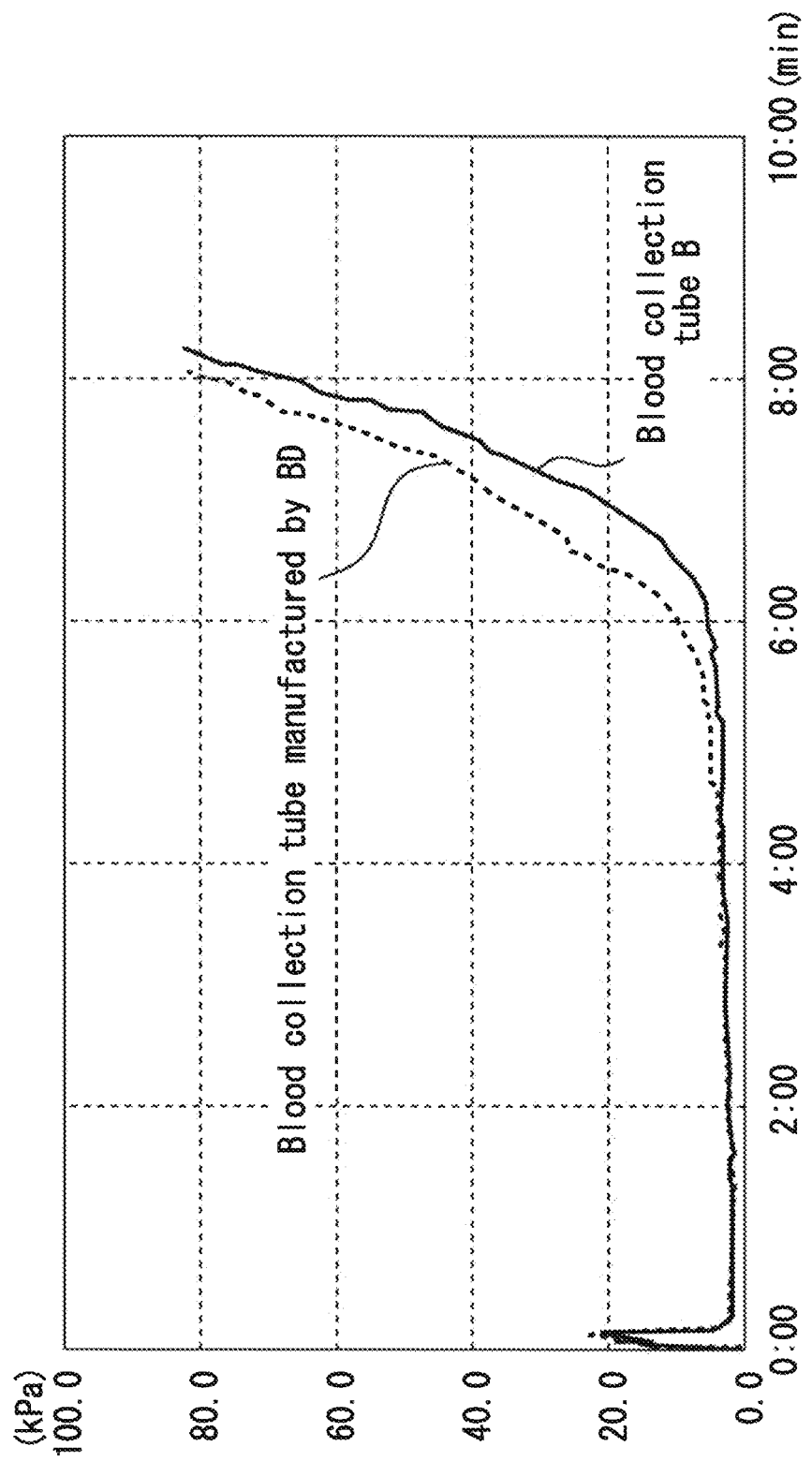
FIG. 11 is a diagram illustrating the results of measurement of white thrombus formation that was carried out by adding calcium chloride and CTI to blood collected using a blood collection tube B, and the results of measurement of white thrombus formation that was carried out by adding calcium chloride, CTI, aprotinin, and heparin sodium to blood collected using a blood collection tube manufactured by BD; Example 8.

The results are shown in FIG. 11.

Similarly to the blood collection tube having a film seal manufactured by Terumo Corporation, the blood collection tube having a butyl rubber stopper manufactured by BD enabled measurement of the white thrombus formation capacity.

Example 9

Figure 12A:
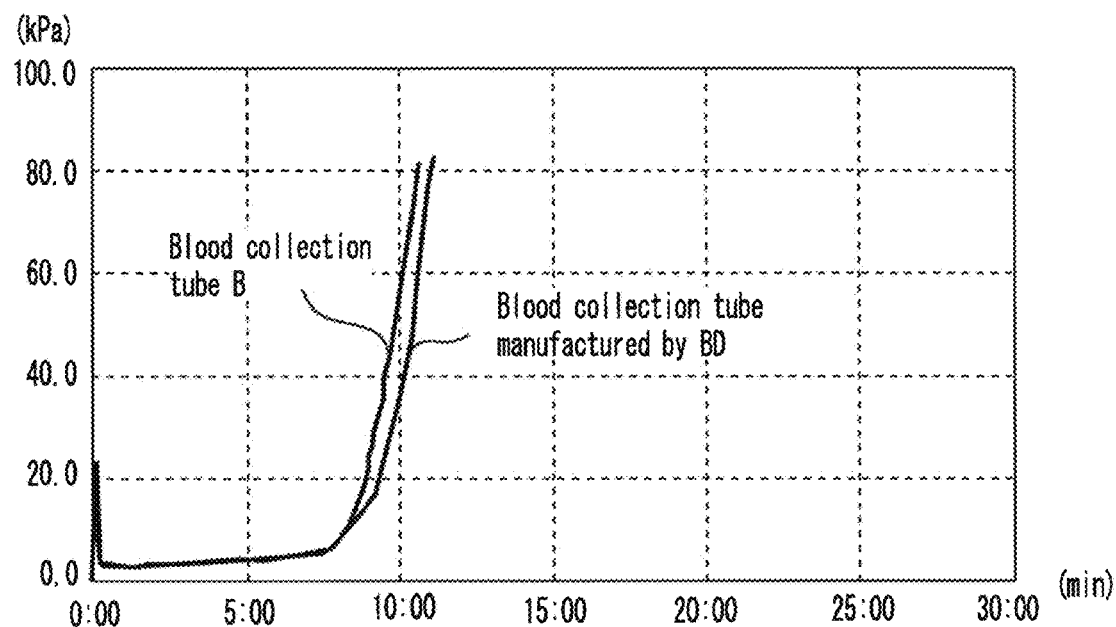
FIG. 12A is a diagram illustrating the results of measurement of white thrombus formation that was carried out by adding calcium chloride and CTI to blood collected using a blood collection tube B, and the results of measurement of white thrombus formation that was carried out by adding calcium chloride, CTI, aprotinin, and heparin sodium to blood collected using a blood collection tube manufactured by BD.

A) A blood sample prepared by adding calcium chloride (final concentration, 12 mM) and CTI (final concentration, 50 µg/mL) to blood collected in a blood collection tube B (sealed with a film seal, without use of a rubber stopper; containing 3.2% sodium citrate; manufactured by Terumo Corporation) and B) a blood sample prepared by adding calcium chloride (final concentration, 12 mM), CTI (final concentration, 50 µg/mL), aprotinin (final concentration, 20 µg/mL), and heparin sodium (final concentration, 0.15 U/mL) to blood collected in a sodium citrate blood collection tube manufactured by BD (containing 3.2% sodium citrate in an amount of 1/10 volume with respect to the blood) were used to perform analysis of the thrombogenic capacity using the device of FIG. 2. The analysis was carried out at a flow rate of 10 µL/min. (FIG. 12A).

Further, an anticoagulant rivaroxaban or dabigatran was added to each of samples A) and B) at 0 nM, 500 nM, or 1000 nM, and measurement was carried out in the same manner.

Figure 12B:
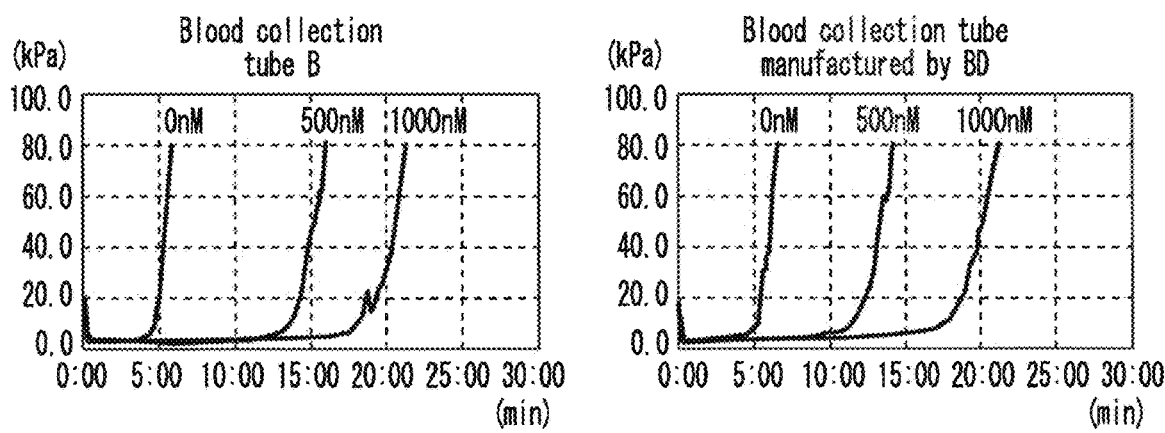
FIG. 12B is a diagram illustrating the results of measurement of white thrombus formation that was carried out by adding calcium chloride and CTI to blood collected using a blood collection tube B, and the results of measurement of white thrombus formation that was carried out by adding calcium chloride, CTI, aprotinin, and heparin sodium to blood collected using a blood collection tube manufactured by BD.
Figure 12C:
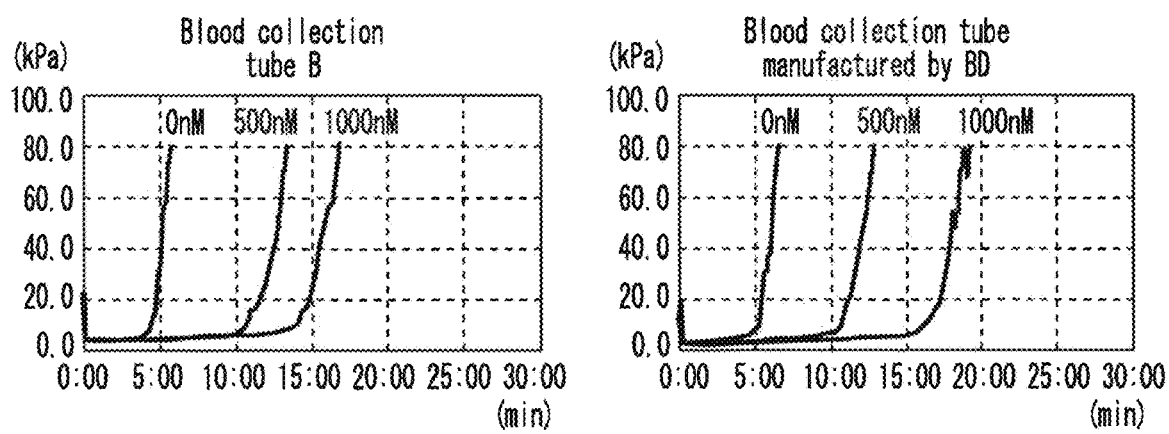
FIG. 12C is a diagram illustrating the results of measurement of white thrombus formation that was carried out by adding calcium chloride and CTI to blood collected using a blood collection tube B, and the results of measurement of white thrombus formation that was carried out by adding calcium chloride, CTI, aprotinin, and heparin sodium to blood collected using a blood collection tube manufactured by BD.

The results for rivaroxaban and dabigatran are shown in FIG. 12B and FIG. 12C, respectively.

As a result, the antithrombogenic effects of the anticoagulants could be sensitively measured for sample B) similarly to sample A).

Example 10

To a blood sample collected in a sodium citrate blood collection tube manufactured by BD (containing 3.2% sodium citrate in an amount of 1/10 volume with respect to the blood), the following reagents were added to perform ROTEM measurement.

(1) Calcium chloride (final concentration, 12 mM), CTI (final concentration, 50 µg/mL), aprotinin (final concentration, 20 µg/mL), heparin sodium (final concentration, 0.15 U/mL), and a prothrombin reagent (addition of HemosIL RecombiPlasTin (15 µg/mL) to a final concentration of about 0.04%)

(2) Calcium chloride (final concentration, 12 mM), CTI (final concentration, 50 µg/mL), aprotinin (final concentration, 20 µg/mL), heparin sodium (final concentration, 0.15 U/mL), NovoSeven (final concentration, 2 µg/mL), and a prothrombin reagent (addition of HemosIL RecombiPlasTin to a final concentration of 0.04%)

(3) Calcium chloride (final concentration, 12 mM), CTI (final concentration, 50 µg/mL), aprotinin (final concentration, 20 µg/mL), heparin sodium (final concentration, 0.15 U/mL), a tissue factor pathway inhibitor (TFPI) (Ac-FQSKpNVHVDGYFERLXAKL-$NH_2$; N-terminal acetylated, C-terminal amidated, p at the 5th position=D-Pro residue, X at the 17th position=Aib (α-methyl alanine); J Biol Chem. 2014 Jan. 17; 289(3): 1732-41; final concentration, 10 µg/mL), and a prothrombin reagent (addition of HemosIL RecombiPlasTin to a final concentration of 0.04%)

Figure 13:
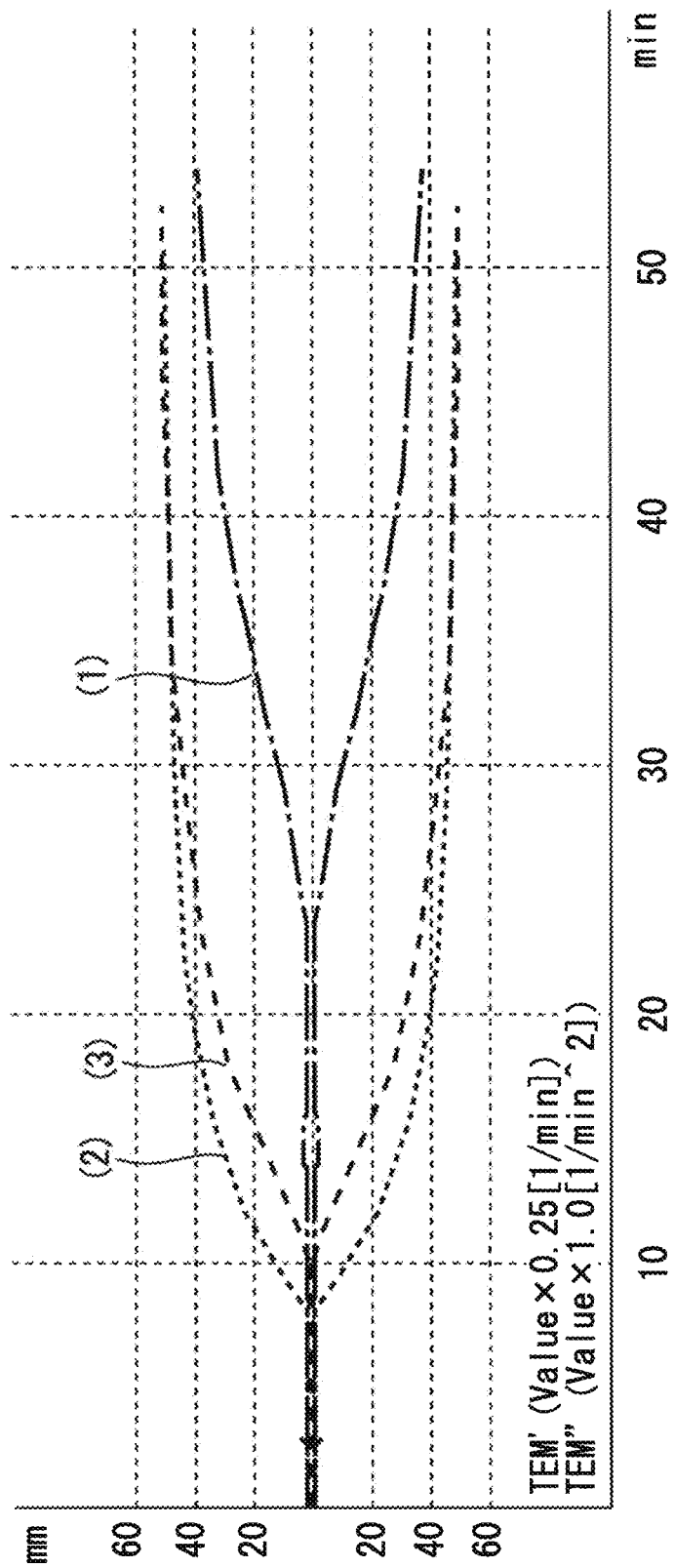
FIG. 13 is a diagram illustrating the results of ROTEM measurement that was carried out by adding each reagent to blood collected in a sodium citrate blood collection tube manufactured by BD; Example 10.

The results are shown in FIG. 13. Coagulation occurred in the order of (2), (3), and (1), as can be seen from left to right.

Comparative Example

To a blood sample collected in a sodium citrate blood collection tube manufactured by BD (containing 3.2% sodium citrate in an amount of 1/10 volume with respect to the blood), the following reagents were added to perform ROTEM measurement.

(1) STARTEM reagent and EXTEM reagent (trademark; a test reagent containing tissue factor as a major component)

(2) STARTEM reagent, EXTEM reagent, and NovoSeven (Novo Nordisk Pharma Ltd.; final concentration, 2 µg/mL)

(3) STARTEM reagent, EXTEM reagent, and TFPI (final concentration, 10 µg/mL)

Figure 14:
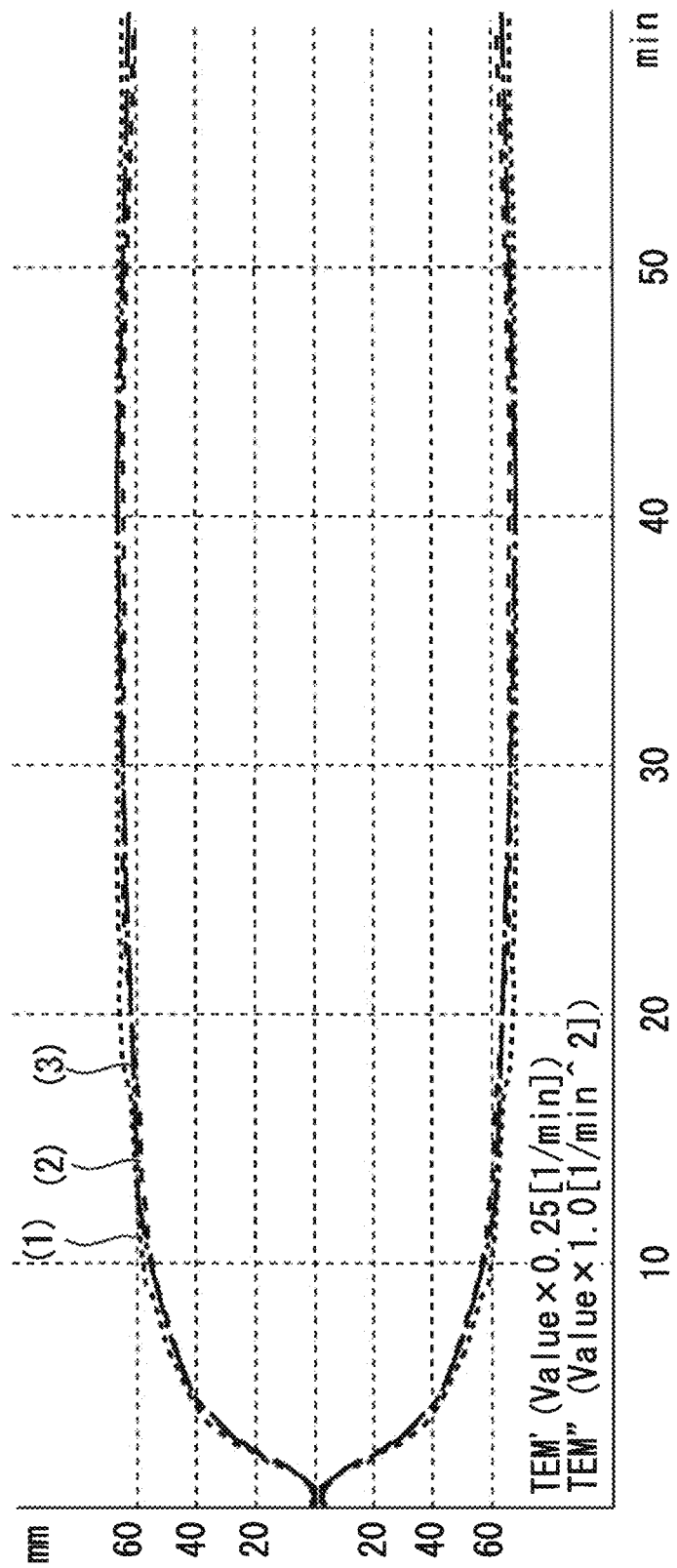
FIG. 14 is a diagram illustrating the results of ROTEM measurement that was carried out by adding each reagent to blood collected in a sodium citrate blood collection tube manufactured by BD; Comparative Example.

The results are shown in FIG. 14. (1), (2), and (3) showed the same waveform.

According to the Examples and the Comparative Example, evaluation of the effects of hemostatic preparations such as NovoSeven and TFPI was possible with the systems in which tissue factor was added together with calcium chloride, aprotinin, and heparin. In contrast, the EXTEM reagent system failed the evaluation.

Example 11

A blood sample prepared by adding calcium chloride (final concentration, 12 mM), CTI (final concentration, 50 µg/mL), aprotinin (final concentration, 20 µg/mL), and danaparoid sodium (final concentration, 0.05 U/mL) to blood collected in a sodium citrate blood collection tube manufactured by BD (containing 3.2% sodium citrate in an amount of 1/10 volume with respect to the blood) was used to perform analysis of the thrombogenic capacity using the device of FIG. 2. The analysis was carried out at a flow rate of 10 µL/min.

Blood prepared by further adding dabigatran (1000 nM) or Abciximab (antiplatelet agent; trade name, ReoPro) (2 µg/mL) to the above blood was used to perform the same experiment.

Figure 15:
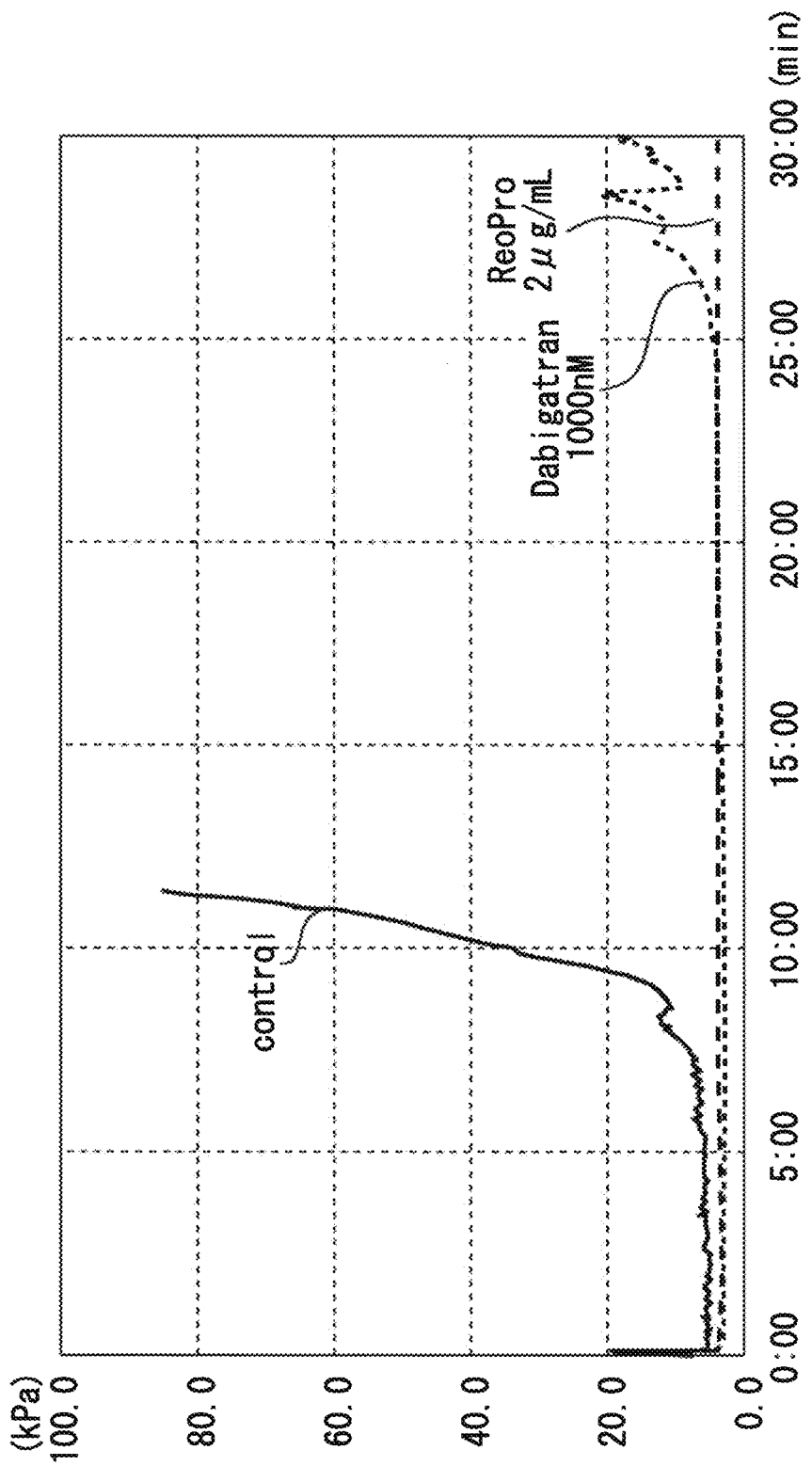
FIG. 15 is a diagram illustrating the results of measurement of white thrombus formation that was carried out by adding calcium chloride, CTI, aprotinin, and danaparoid sodium to blood collected using a sodium citrate blood collection tube manufactured by BD; Example 11.

The results are shown in FIG. 15. With a blood collection tube having a butyl rubber stopper manufactured by BD, measurement of the white thrombus formation capacity and evaluation of the anticoagulant and the antiplatelet agent were possible.

Example 12

Calcium chloride (final concentration, 12 mM), CTI (final concentration, 50 µg/mL), aprotinin (final concentration, 20 µg/mL), and danaparoid sodium (final concentration, 0.05 U/mL) were added to a blood sample collected in a sodium citrate blood collection tube manufactured by BD (containing 3.2% sodium citrate in an amount of 1/10 volume with respect to the blood), and the blood sample was then subjected to ROTEM measurement.

Further, recombinant factor VIIa (trade name, NovoSeven) (0.5 μg/mL) or TFPI (50 μg/mL), or their combination was added to the blood, and the blood was then subjected to the measurement.

Figure 16:
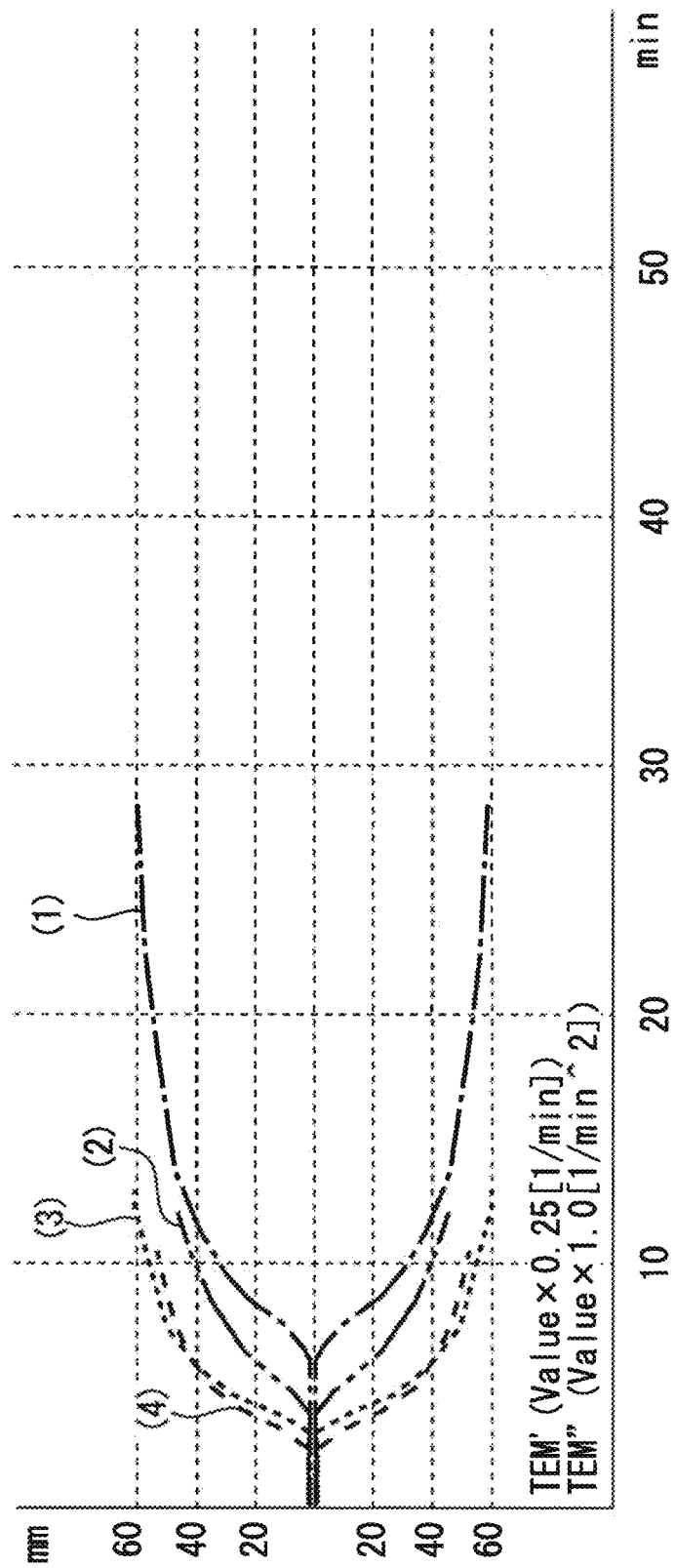
FIG. 16 is a diagram illustrating the results of ROTEM measurement that was carried out by adding calcium chloride, CTI, aprotinin, and danaparoid sodium to blood collected in a sodium citrate blood collection tube manufactured by BD; Example 12.

The results are shown in FIG. 16. In FIG. 16, (1) represents addition of neither NovoSeven nor TFPI; (2) represents only NovoSeven; (3) represents only TFPI; and (4) represents NovoSeven+TFPI.

As a result, the ROTEM measurement and judgment of the effects of the hemostatic preparations were possible with the sodium citrate blood collection tube manufactured by BD.

Example 13

Calcium chloride (final concentration, 12 mM), CTI (final concentration, 50 μg/mL), aprotinin (final concentration, 20 μg/mL), and danaparoid sodium (final concentration, 0.05 U/mL) were added to a blood sample collected in a sodium citrate blood collection tube manufactured by BD (containing 3.2% sodium citrate in an amount of 1/10 volume with respect to the blood), and the blood sample was then subjected to ROTEM measurement.

Further, an anti-FVIII polyclonal antibody (FVIII inhibition activity; 96 μg/mL; 218 BU (FVIII inhibition activity units)), and NovoSeven (0.5 μg/mL) or TFPI (50 μg/mL) or their combination, were added to the blood, and the blood was then subjected to the measurement.

Figure 17:
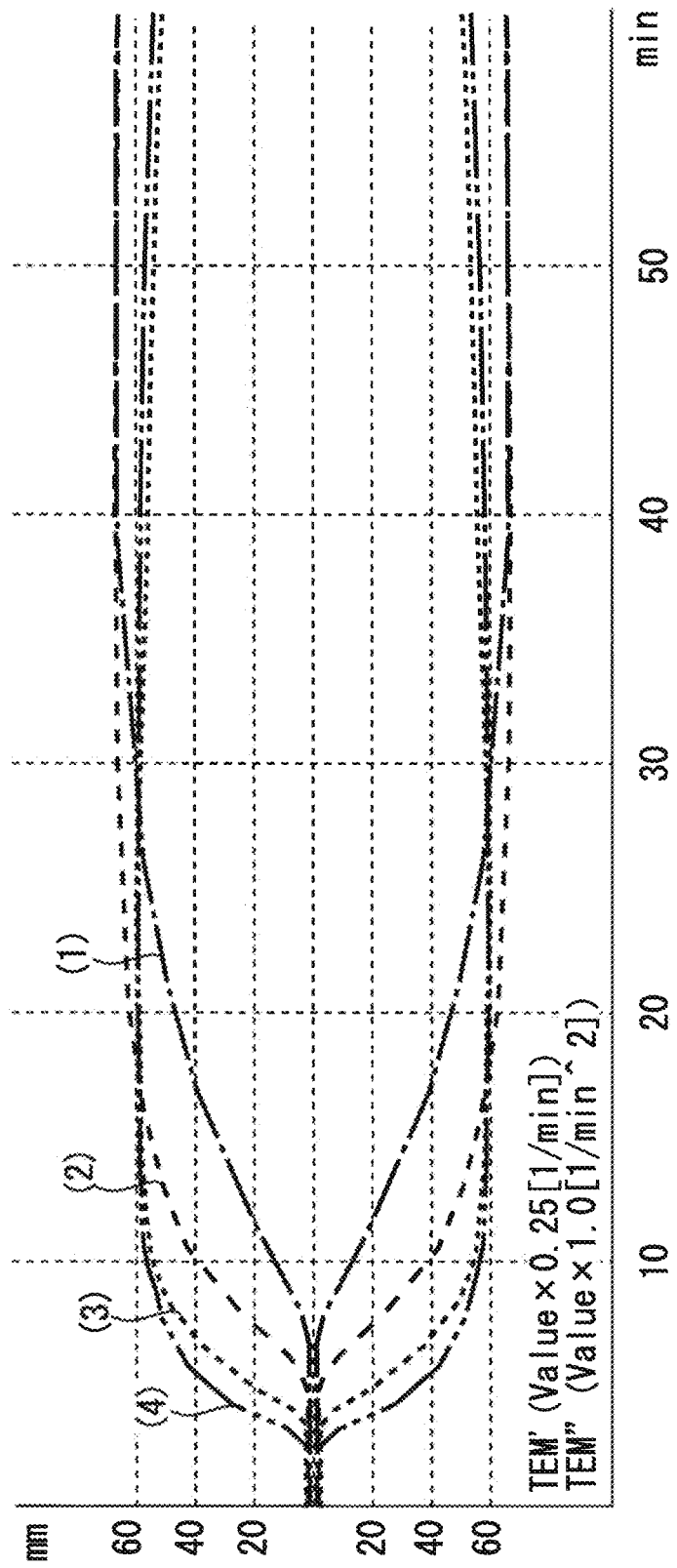
FIG. 17 is a diagram illustrating the results of ROTEM measurement that was carried out by adding calcium chloride, CTI, aprotinin, and danaparoid sodium to blood collected in a sodium citrate blood collection tube manufactured by BD; Example 13.

The results are shown in FIG. 17. In FIG. 17, (1) represents only the anti-FVIII polyclonal antibody; (2) represents the anti-FVIII polyclonal antibody+NovoSeven; (3) represents the FVIII polyclonal antibody+TFPI; and (4) represents the FVIII polyclonal antibody+NovoSeven+TFPI.

The ROTEM measurement and judgment of the effects of the hemostatic preparations were possible with the sodium citrate blood collection tube manufactured by BD.

DESCRIPTION OF SYMBOLS

A . . . microchip; 101, 111 . . . channel; 102,112 . . . reaction section; 103, 113 . . . waste liquid storage section; 104, 114 . . . inlet; 105, 115 . . . waste liquid outlet; 106, 116 . . . reservoir; 107, 117 . . . liquid transfer pump; 108, 118 . . . pressure sensor B . . . microchip; 201 . . . channel; 202 . . . reaction section; 203 . . . waste liquid storage section; 204 . . . inlet; 205 . . . waste liquid outlet; 206 . . . reservoir; 207 . . . liquid transfer pump; 208 . . . pressure sensor; 209 . . . narrow section; 210 . . . blood coagulation inhibitor channel; 211 . . . blood coagulation inhibitor inlet

What is claimed is:

1. A method for analyzing thrombogenic capacity or blood coagulation capacity, the method comprising adding calcium, a blood coagulation factor XII (FXII) inhibitor, a kallikrein inhibitor, heparin or heparan sulfate, and tissue factor to blood collected with a blood collection tube having a butyl rubber stopper and containing sodium citrate, to allow initiation of a blood coagulation reaction, and then analyzing thrombogenic capacity or blood coagulation capacity using the blood.

2. The method for analyzing thrombogenic capacity or blood coagulation capacity according to claim 1, wherein the FXII inhibitor is corn-derived trypsin inhibitor (CTI).

3. The method for analyzing thrombogenic capacity or blood coagulation capacity according to claim 2, wherein the concentration of CTI is 5 μg/mL to 50 μg/mL.

4. The method for analyzing thrombogenic capacity or blood coagulation capacity according to claim 1, wherein the kallikrein inhibitor is aprotinin.

5. The method for analyzing thrombogenic capacity or blood coagulation capacity according to claim 4, wherein the concentration of aprotinin is 1 μg/mL to 50 μg/mL.

6. The method for analyzing thrombogenic capacity or blood coagulation capacity according to claim 1, wherein the heparin is a low-molecular-weight heparin having a mass average molecular weight of 4500 to 6500.

7. The method for analyzing thrombogenic capacity or blood coagulation capacity according to claim 1, wherein the heparan sulfate is danaparoid sodium.

8. The method for analyzing thrombogenic capacity or blood coagulation capacity according to claim 1, wherein the tissue factor is recombinant soluble tissue factor and the concentration of the recombinant soluble tissue factor is 0.1 nM to 10 nM.

9. The method for analyzing thrombogenic capacity or blood coagulation capacity according to claim 1, comprising analyzing the blood coagulation capacity by ROTEM.

10. A method for analyzing thrombogenic capacity or blood coagulation capacity, the method comprising adding calcium, a blood coagulation factor XII (FXII) inhibitor, a kallikrein inhibitor, and heparin or heparan sulfate to blood collected with a blood collection tube having a butyl rubber stopper and containing sodium citrate, to allow initiation of a blood coagulation reaction, and then analyzing thrombogenic capacity or blood coagulation capacity using the blood, said analysis comprising allowing the blood to flow through a channel(s) mimicking a blood vessel(s) and having a portion coated with collagen and tissue factor provided in a microchip, to analyze mixed white thrombus formation capacity.

11. The method for analyzing thrombogenic capacity or blood coagulation capacity according to claim 10, wherein the FXII inhibitor is corn-derived trypsin inhibitor (CTI).

12. The method for analyzing thrombogenic capacity or blood coagulation capacity according to claim 11, wherein the concentration of CTI is 5 μg/mL to 50 μg/mL.

13. The method for analyzing thrombogenic capacity or blood coagulation capacity according to claim 10, wherein the kallikrein inhibitor is aprotinin.

14. The method for analyzing thrombogenic capacity or blood coagulation capacity according to claim 13, wherein the concentration of aprotinin is 1 μg/mL to 50 μg/mL.

15. The method for analyzing thrombogenic capacity or blood coagulation capacity according to claim 10, wherein the heparin is a low-molecular-weight heparin having a mass average molecular weight of 4500 to 6500.

16. The method for analyzing thrombogenic capacity or blood coagulation capacity according to claim 10, wherein the heparan sulfate is danaparoid sodium.

17. The method for analyzing thrombogenic capacity or blood coagulation capacity according to claim 10, wherein the tissue factor is recombinant soluble tissue factor and the concentration of the recombinant soluble tissue factor is 0.1 nM to 10 nM.

18. A method for analyzing thrombogenic capacity or blood coagulation capacity, the method comprising adding calcium, corn-derived trypsin inhibitor as a blood coagulation factor XII (FXII) inhibitor, aprotinin as a kallikrein inhibitor, heparin or heparan sulfate, and tissue factor to blood collected with a blood collection tube having a butyl rubber stopper and containing sodium citrate, to allow initiation of blood coagulation reaction, and then analyzing thrombogenic capacity or blood coagulation capacity using the blood.

19. The method for analyzing thrombogenic capacity or blood coagulation capacity according to claim 18, wherein the tissue factor is recombinant soluble tissue factor and the concentration of the recombinant soluble tissue factor is 0.1 nM to 10 nM.

* * * * *